(12) United States Patent
Martini et al.

(10) Patent No.: US 9,952,033 B2
(45) Date of Patent: Apr. 24, 2018

(54) SPATIAL MODULATION OF LIGHT TO DETERMINE OBJECT LENGTH

(71) Applicant: Palo Alto Research Center Incorporated, Palo Alto, CA (US)

(72) Inventors: Joerg Martini, San Francisco, CA (US); Marshall W. Bern, San Carlos, CA (US); Noble M. Johnson, Menlo Park, CA (US); Peter Kiesel, Palo Alto, CA (US); Doron Kletter, San Mateo, CA (US); Bowen Cheng, Atherton, CA (US); Michael I. Recht, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 919 days.

(21) Appl. No.: 14/181,530

(22) Filed: Feb. 14, 2014

(65) Prior Publication Data
US 2015/0233703 A1 Aug. 20, 2015

(51) Int. Cl.
*G01C 3/08* (2006.01)
*G01B 11/04* (2006.01)
(Continued)

(52) U.S. Cl.
CPC ....... *G01B 11/043* (2013.01); *G01N 15/1459* (2013.01); *G01P 3/36* (2013.01);
(Continued)

(58) Field of Classification Search
CPC ............ G01B 11/043; G01N 15/1459; G01N 2015/1447; G01N 2015/1493; G01P 3/36; G01P 15/00
See application file for complete search history.

(56) References Cited

U.S. PATENT DOCUMENTS 4,037,965 A   7/1977 Weiss
4,172,227 A   10/1979 Tyrer et al.
(Continued)

FOREIGN PATENT DOCUMENTS

EP      1950552       7/2008
WO      WO0194938    12/2001
WO      WO2005017969  2/2005

OTHER PUBLICATIONS

File History for EP App. No. 15153858.4 as retrieved from the EP Electronic File System on Aug. 5, 2016, 117 pages.
(Continued)

*Primary Examiner* — Samantha K Abraham
(74) *Attorney, Agent, or Firm* — Hollingsworth Davis, LLC

(57) ABSTRACT

Spatially modulated light emanating from an object moving along a flow path is used to determine various object characteristics including object length along the flow direction. Light emanating from at least one object moving along in a flow path along a flow direction of a spatial filter is sensed. The intensity of the sensed light is time modulated according to features of the spatial filter. A time varying electrical signal is generated which includes a plurality of pulses in response to the sensed light. Pulse widths of at least some of the pulses are measured at a fraction of a local extremum of the pulses. The length of the object along the flow direction is determined based on the measured pulse widths.

29 Claims, 22 Drawing Sheets

(51) Int. Cl.
*G01P 3/36* (2006.01)
*G01P 15/00* (2006.01)
*G01N 15/14* (2006.01)

(52) U.S. Cl.
CPC ...... *G01P 15/00* (2013.01); *G01N 2015/1447* (2013.01); *G01N 2015/1493* (2013.01)

(56) References Cited

U.S. PATENT DOCUMENTS

| | | |
|---|---|---|
| 4,441,816 A | 4/1984 | Hencken et al. |
| 4,596,254 A | 6/1986 | Adrian et al. |
| 5,392,776 A | 2/1995 | Thurston et al. |
| 5,682,038 A | 10/1997 | Hoffman |
| 5,778,878 A | 7/1998 | Kellam |
| 6,213,579 B1 | 4/2001 | Cornell et al. |
| 6,649,416 B1 | 11/2003 | Kauer et al. |
| 6,654,521 B2 | 11/2003 | Sheng et al. |
| 7,104,634 B2 | 9/2006 | Weksler et al. |
| 7,291,824 B2 | 11/2007 | Kiesel et al. |
| 7,358,476 B2 | 4/2008 | Kiesel et al. |
| 7,386,199 B2 | 6/2008 | Schmidt et al. |
| 7,420,677 B2 | 9/2008 | Schmidt et al. |
| 7,471,393 B2 | 12/2008 | Trainer |
| 7,471,399 B2 | 12/2008 | Kiesel et al. |
| 7,479,625 B2 | 1/2009 | Kiesel et al. |
| 7,502,123 B2 | 3/2009 | Kiesel et al. |
| 7,547,904 B2 | 6/2009 | Schmidt et al. |
| 7,688,427 B2 | 3/2010 | Cox et al. |
| 7,701,580 B2 | 4/2010 | Bassler et al. |
| 7,763,856 B2 | 7/2010 | Kiesel et al. |
| 7,817,254 B2 | 10/2010 | Hegyi et al. |
| 7,817,276 B2 | 10/2010 | Kiesel et al. |
| 7,894,068 B2 | 2/2011 | Bassler et al. |
| 7,961,326 B2 | 6/2011 | Martini et al. |
| 8,082,015 B2 | 12/2011 | Yodh et al. |
| 8,153,949 B2 | 4/2012 | Kiesel et al. |
| 8,153,950 B2 | 4/2012 | Kiesel et al. |
| 8,203,711 B2 | 6/2012 | Shinoda |
| 8,373,860 B2 | 2/2013 | Kiesel et al. |
| 8,388,569 B2 | 3/2013 | Uhland et al. |
| 8,437,582 B2 | 5/2013 | Kiesel |
| 8,594,470 B2 | 11/2013 | Kiesel et al. |
| 8,629,981 B2 | 1/2014 | Martini et al. |
| 8,842,259 B2 | 9/2014 | Garey |
| 8,921,277 B2 | 12/2014 | Kiesel et al. |
| 9,074,978 B2 | 7/2015 | Lo et al. |
| 9,114,606 B1 | 8/2015 | Ready et al. |
| 9,134,221 B2 | 9/2015 | Lo et al. |
| 9,207,066 B2 | 12/2015 | Martini et al. |
| 9,261,452 B2 | 2/2016 | Martini et al. |
| 9,629,981 B2 | 4/2017 | Thungana et al. |
| 2003/0203502 A1 | 10/2003 | Zenhausern et al. |
| 2003/0235924 A1 | 12/2003 | Adams et al. |
| 2004/0067137 A1 | 4/2004 | Moroso |
| 2004/0226386 A1 | 11/2004 | Gysling et al. |
| 2007/0076210 A1 | 4/2007 | Kiesel et al. |
| 2007/0145249 A1 | 6/2007 | Kiesel et al. |
| 2007/0146704 A1 | 6/2007 | Schmidt et al. |
| 2007/0146888 A1 | 6/2007 | Schmidt et al. |
| 2007/0147728 A1 | 6/2007 | Schmidt et al. |
| 2008/0181827 A1 | 7/2008 | Bassler et al. |
| 2008/0183418 A1 | 7/2008 | Bassler et al. |
| 2008/0186488 A1 | 8/2008 | Kiesel et al. |
| 2008/0186492 A1 | 8/2008 | Kiesel et al. |
| 2008/0186504 A1 | 8/2008 | Kiesel et al. |
| 2009/0156917 A1 | 6/2009 | Martini et al. |
| 2009/0190121 A1 | 7/2009 | Hegyi et al. |
| 2009/0195773 A1 | 8/2009 | Kiesel et al. |
| 2010/0201988 A1 | 8/2010 | Kiesel |
| 2010/0225913 A1* | 9/2010 | Trainer ............. G01N 15/0205 356/338 |
| 2012/0194590 A1 | 8/2012 | Suzuki |
| 2012/0236291 A1 | 9/2012 | Pittaro et al. |
| 2013/0016335 A1 | 1/2013 | Lo et al. |
| 2013/0037726 A1 | 2/2013 | Kiesel et al. |
| 2013/0037728 A1 | 2/2013 | Kiesel et al. |
| 2013/0083315 A1 | 4/2013 | Lo |
| 2014/0152986 A1 | 6/2014 | Trainer |
| 2014/0192359 A1 | 7/2014 | Martini |
| 2014/0370612 A1 | 12/2014 | Kiesel et al. |
| 2015/0105295 A1 | 4/2015 | Kiesel et al. |
| 2015/0177118 A1 | 6/2015 | Johnson et al. |
| 2015/0185139 A1 | 7/2015 | Kiesel et al. |
| 2015/0233703 A1 | 8/2015 | Martini et al. |
| 2015/0276387 A1 | 10/2015 | Kletter et al. |
| 2015/0276486 A1 | 10/2015 | Martini et al. |
| 2015/0280290 A1 | 10/2015 | Saha et al. |

OTHER PUBLICATIONS

File History for U.S. Appl. No. 14/181,560.
File History for U.S. Appl. No. 14/181,524.
U.S. Appl. No. 14/155,094, filed Jan. 14, 2014, Martini et al.
Kiesel et al., "Spatially Modulated Fluorescence Emission from Moving Particles", Appl. Phys. Lett. 94, 2009, pp. 041107-1-041107-3.
Kiesel et al., "Spatially Modulated Emission Advances Point-of-Care Diagnostics", Laser Focus World, Nov. 2010, pp. 47-50.
Petersson et al., "Free Flow Acoustophoresis: Micorfluidic-Based Mode of Particle and Cell Separation", Anal. Chem, 79 (14), 2007, pp. 5117-5123.
Yamada et al., "Pinched flow fractionation: continuous size separation of particles utilizing a laminar flow profile in a pinched microchannel", Anal. Chem. 76 (18), Sep. 2004, pp. 5465-5471. (abstract only).
Yamada et al., "Microfluidic Particle Sorter Employing Flow Splitting and Recombining", Anal. Chem. 78, 2006, pp. 1357-1362.
Ji et al., "Silicon-based microfilters for whole blood cell separation", Biomed Microdevices 10(2), 2008, pp. 251-257. (abstract only).
Schrum et al., "Microchip Flow Cytometry Using Electrokinetic Focusing", Anal. Chem. 71 (19), Oct. 1999, pp. 4173-4177. (abstract only).
Huh et al., "Microfluidics for flow cytometric analysis of cells and particles" Physiol. Meas. 26 (3), Jun. 2005, pp. R73-R98. (abstract only).
Fu et al., "Electrokinetically driven micro flow cytometers with integrated fiber optics for on-line cell/particle detection", Analytica Chimica Acta, Vo. 507 (1), Apr. 2004, pp. 163-169. (abstract only).
Lee, Gwo-Bin et al., "Micromachine-based multi-channel flow cytometers for cell/particle counting and sorting", J. Micromech, Microeng. 15 (2005) 447-454. (abstract only).
Lin et al., "Vertical focusing device utilizing dielectrophoratic force and its application on microflow cytometer", Journal of Microelectromechanical Systems, vol. 13, No. 6, Dec. 2004, 10 pages.
Zhu et al., "Dielectrophoretic focusing of particles in a microchannel constriction using DC-biased AC flectric fields", Electrophoresis, vol. 30 (15), Jul. 2009. (abstract only).
Chu et al., "A three-dimensional (3D) particle focusing channel using the positive dielectrophoresis (pDEP) guided by a dielectric structure between two planar electrodes", Lab on a Chip, Issue 5m 2009, pp. 688-691. (abstract only).
Chang et al., Three-dimensional hydrodynamic focusing in two-layer polydimethylsiloxane (PDMS) microchannels, J. Michromech. Microeng 17, 2007, pp. 1479-1486.
Sheng et al., "Digital holographic microscope for measuring three-dimensional particle distributions and motions", Applied Optics, Vo. 45 (16), Jun. 2006, pp. 3893-3901.
Lindken et al., "Stereoscopic micro particle image velocimetry" Experiments in Fluids, 41, 2006, pp. 161-171.
Pereira et al., "Microscale 3D flow mapping with μDDPIV", Experiments in Fluids, vol. 42 (4), Apr. 2007, pp. 589-599. (abstract only).
Cheong et al., "Flow Visualizaiton and Flow Cytometry with Holographic Video Microscopy", Optics Express 17, 2009, pp. 13071-13079.

(56) References Cited

OTHER PUBLICATIONS

Lima et al., "Confocal micro-PIV measurements of three dimensional profiles of cell suspension flow in a square microchannel", Measurement Science and Technology, vol. 17, 2006, pp. 797-808.
Pugia et al., "Microfluidic Tool Box as Technology Platform for Hand-Held Diagnostics", Clinical Chemistry, vol. 51 (10), 2005, pp. 1923-1932.
File History for U.S. Appl. No. 13/206,436.
File History for U.S. Appl. No. 12/024,490.
File History for U.S. Appl. No. 12/762,702.
File History for U.S. Appl. No. 13/113,021.
File History for U.S. Appl. No. 14/246,893.
File History for U.S. Appl. No. 14/246,912.
U.S. Appl. No. 14/181,560, filed Feb. 14, 2014, Kletter et al.
U.S. Appl. No. 14/181,571, filed Feb. 14, 2014, Martini et al.
U.S. Appl. No. 14/181,524, filed Feb. 14, 2014, Martini et al.
File History for U.S. Appl. No. 15/209,450.
File History for U.S. Appl. No. 14/181,571.

* cited by examiner

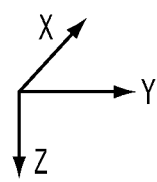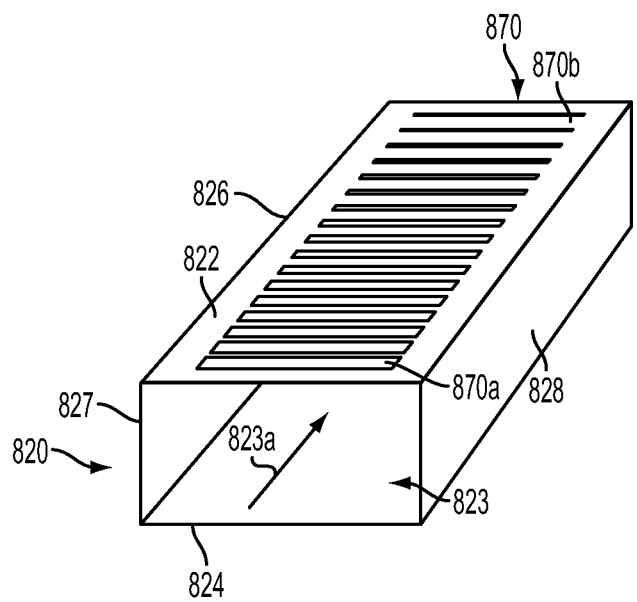
FIG. 8A

SPATIAL MODULATION OF LIGHT TO DETERMINE OBJECT LENGTH

STATEMENT REGARDING FEDERALLY SPONSORED RESEARCH AND DEVELOPMENT

This invention was made with government support under contract number W911NF-10-1-0479 (3711), awarded by the Department of Defense. The U.S. Government has certain rights in this invention.

TECHNICAL FIELD

This application relates generally to techniques for performing sample analysis by evaluating light emanating from the objects in a sample. The application also relates to components, devices, systems, and methods pertaining to such techniques.

BACKGROUND

The present disclosure relates generally to techniques that determine object characteristics using light emanating from the objects. More specifically, the techniques can use filter arrangements to transmit and/or reflect light with time variation, such as where the objects are moving relative to the filter arrangements.

Various techniques have been proposed for using light emanating from objects. For example, U.S. Pat. No. 7,358,476 (Kiesel et al.) describes a fluidic structure with a channel along which is a series of sensing components to obtain information about objects traveling within the channel, such as droplets or other objects carried by fluid. A sensing component includes a set of cells that photosense a range of photon energies that emanate from objects. A processor can receive information about objects from the sensing components and use it to obtain spectral information. Additional techniques are described, for example, in U.S. Patent Application Publications 2008/0181827 (Bassler et al.) and 2008/0183418 (Bassler et al.) and in U.S. Pat. No. 7,701,580 (Bassler et al.), U.S. Pat. No. 7,894,068 (Bassler et al.), U.S. Pat. No. 7,547,904 (Schmidt et al.), U.S. Pat. No. 8,373,860 (Kiesel et al.), U.S. Pat. No. 7,420,677 (Schmidt et al.), and U.S. Pat. No. 7,386,199 (Schmidt et al.).

Also, various flow cytometry techniques have been proposed.

SUMMARY

Some embodiments described herein relate to a system configured to spatially modulate light and to determine various characteristics of objects based on the spatially modulated light. The system includes a spatial filter having a plurality of mask features disposed along a longitudinal axis of the filter. A detector is positioned to sense light emanating from at least one object moving in a flow path along a flow direction that corresponds to the longitudinal axis of the filter. As the intensity of the sensed light is modulated according to the mask features the detector generates a time varying electrical signal comprising a sequence of time modulated pulses responsive to the sensed light. The system includes an analyzer configured to measure a pulse width of at least some of the pulses at a fraction of an amplitude extremum of the pulses. The analyzer determines a length of the object along the flow direction based on the measured pulse widths.

Some embodiments are directed to a method of determining object length. Light emanating from at least one object moving along in a flow path along a flow direction of a spatial filter is sensed. The spatial filter has a plurality of mask features comprising first features alternating with second features along the flow direction. The first features have first light transmission characteristics and the second features having second light transmission characteristics, different from the first light transmission characteristics. An intensity of the sensed light is modulated according to the mask features. A time varying electrical signal is generated which includes a plurality of pulses responsive to the sensed light. A pulse width of at least some of the pulses is measured at a fraction of a local extremum value of the pulses. The length of the object along the flow direction is determined based on the measured pulse widths.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIG. 8A is a perspective view of a portion of a system that includes a spatial filter having mask features that change in length along the flow direction;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
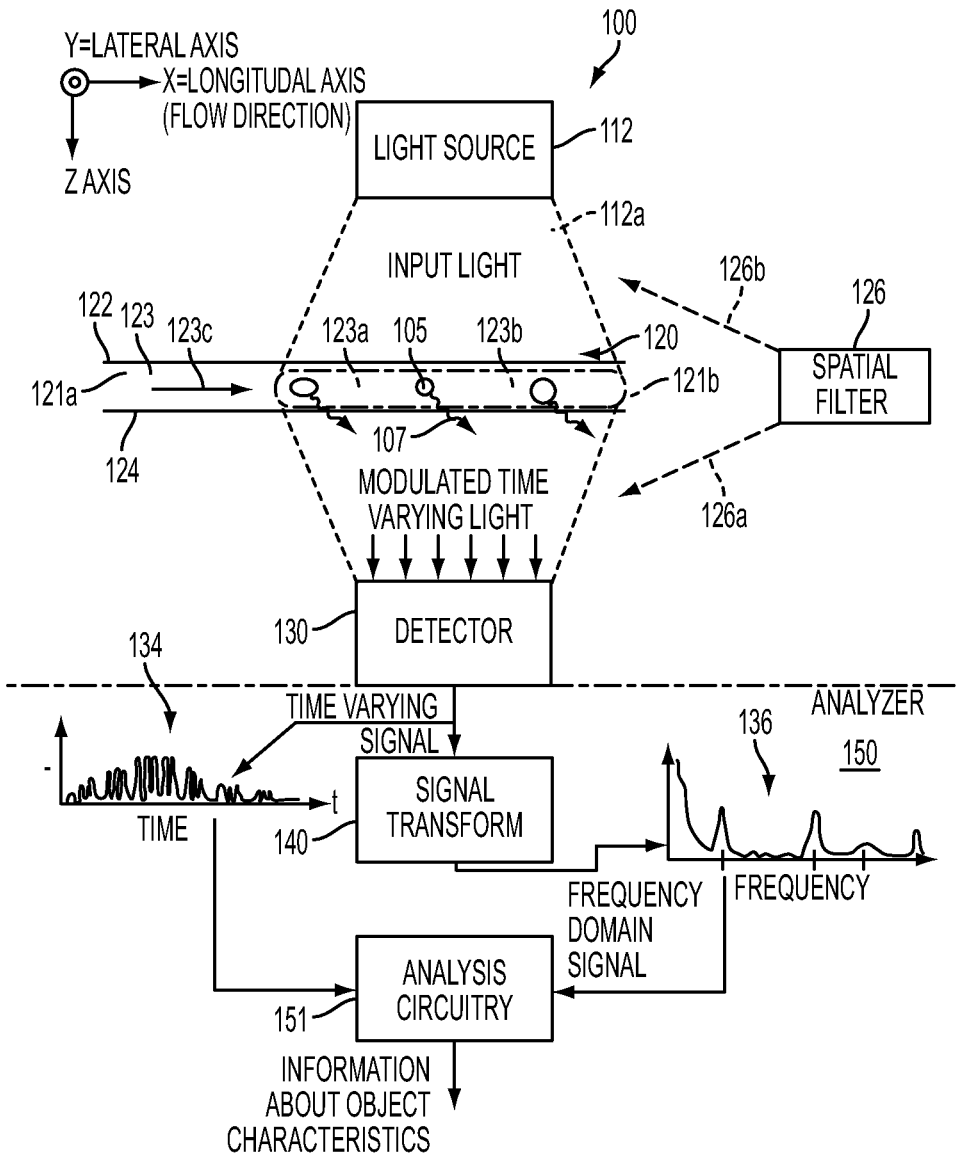
FIG. 1 is an example embodiment of an assembly with a spatial filter, detector, and analyzer configured to determine object characteristics based on spatially modulated light.

The embodiments described herein perform sample analysis to determine the dimensional characteristics of an object, in particular, the length (sometimes referred to as diameter in the case of disc-shaped or spherically-shaped objects) of the object in a flow direction. The determination of dimensional characteristics described herein is based on spatially modulated light emanating from the object. In particular, the techniques disclosed herein make use of at least one spatial filter, also referred to as a mask, that can be deployed in a variety of applications, including analysis of system properties and/or detection of various characteristics of analyte in a sample. In some implementations, a non-imaging photodetector is used to generate a time varying electrical output signal based on the spatially modulated light allowing for compatibility with high-throughput cytometry.

Object length determination approaches described herein involve sensing light emanating from an object moving along an enclosed, partially enclosed or unenclosed flow path. The sensed light is modulated according to features of a mask as the object moves along the flow path along a flow direction of the mask. The mask includes a plurality of mask features comprising first features having first light transmission characteristics alternating with second features having second light transmission characteristics, different from the first light transmission characteristics. As used herein, the terms "first" and "second" identify mask features having differing characteristics and these terms are not meant imply any particular order or arrangement of the mask features. For example, in some implementations, the first mask features are substantially transparent and the second features are substantially opaque. At least one detector is positioned to sense light emanating from at least one object moving in a flow path along the flow direction. An intensity of the sensed light is modulated according to the mask features. The detector generates a time varying electrical signal comprising a plurality of time modulated pulses in response to the sensed light. An analyzer measures the pulse widths of the pulses at a fraction of a local amplitude extremum of the pulses. For example, the local amplitude extremum may be a maximum amplitude for positive going pulses and may be a minimum amplitude for negative going pulses. The analyzer determines one or more characteristics of the object along the flow direction based on the pulse widths, at least one of the characteristics being object length long the direction of flow.

The term "object" refers broadly to any object of interest to be detected. In some applications, objects of interest are particles or analytes that are relatively small, and may be microscopic in size. However, the techniques are broadly applicable to objects of any size or shape. A given object of interest may be or include one or a collection of biological cell(s), virus(es), molecule(s), bead(s) (including microbeads), droplets (e.g. oil in water), gas bubbles, or other bit(s) of matter.

Light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by the detector, e.g., a non-pixelated photodetector. Cells or particles may be treated, e.g., stained or tagged with a suitable fluorescent probe or other agent, in such a way that they emit light or absorb light in a predictable fashion when illuminated with excitation light. In this regard, the light emitted by a given excited particle may be fluorescent in nature, or it may constitute a form of scattered light such as in the case of Raman scattering. For simplicity, the light that emanates from (by e.g., scattering, emission, or transmission) by an object is referred to herein as "emanating light" or "light emanating." It will be understood that the techniques, assemblies, apparatuses, systems, and methods described herein are applicable to detecting all forms of light emanating from an object or constituent parts thereof.

FIG. 1 is an example of an assembly 100 configured to determine object characteristics, such as determining object length according to the approaches discussed herein, based on spatially modulated light. The assembly 100 includes a light source 112, a mask, e.g., a spatial filter 126, a flow path, e.g., fluidic device 120, a detector 130, and an analyzer 150. Optionally, the assembly 100 may include a signal transform module 140, e.g., dedicated circuitry, software or a combination of software and hardware. The signal transform module is configured to convert the time varying signal to the frequency domain, for example, using a Fourier transform.

The fluidic device 120 is adapted to receive a sample of interest to be analyzed. The sample may enter the fluidic device 120 at an inlet 121a thereof and exit the device 120 at an outlet 121b thereof, flowing generally along the x-direction along a flow path 123 which may be formed between confining members 122, 124. The members 122, 124 may be or comprise plates or sheets of glass, plastic, or other suitable materials. One or both of members 122, 124 may be a microscope slide or a microscope cover glass, or portion thereof. The members 122, 124 need not, however, be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122, 124 may be omitted. At least a portion of the confining members 122 and 124 is transmissive to light. A portion of the confining member 122 is transmissive to excitation light emitted by the light source 112 at least in an excitation region 123a. In that regard, light source 112 may emit excitation light 112a towards the flow path 123. Likewise, a portion of the confining member 124 is transmissive to light emanating from the objects 105 at least in an excitation region 123a. In that regard, objects 105 may generate emanating light 107 towards the detector 130.

In some cases, the light source 112 may comprise a conventional light emitting diode (LED) source or a resonant cavity LED (RC-LED) source. If desired, the light source may incorporate one or more filters to narrow or otherwise tailor the spectrum of the resultant output light. Whichever type of light source is selected, the spectral makeup or composition of the excitation light emitted by the source 112 is preferably tailored to excite, scatter, or otherwise cause emanation of light from at least some of the objects that may be present in the sample, as discussed further below.

The sample is depicted as containing exemplary objects 105 of varying sizes and shapes. The objects 105 emanate light 107 in all directions (only some directions are illustrated). The objects 105 may have a variety of characteristics, some of which can be determined by the analyzer 150 based on the emanating light 107.

The detector 130 receives time varying light emanating from the objects 105 as modulated by the spatial filter 126 and generates an electrical signal in response to the time varying light. The time variation in the light detected by the detector 130 may be the result of interaction between the excitation light and an input spatial filter to create spatially patterned excitation light that illuminates the object 105. Alternatively, the time variation in the light detected by the detector 130 may be the result of interaction between light emanating from the objects 105 and an output spatial filter. In some embodiments, the detector includes an additional optical filter arranged between the detector and the objects. An optical filter can be particularly useful when the emanating light is fluorescent light and the optical filter is configured to substantially block the wavelengths of the excitation light and to substantially pass the wavelengths of the light emanating from the objects.

The assembly 100 of FIG. 1 includes the spatial filter 126 (sometimes referred to as a mask) which can be positioned in various locations. Dashed arrows 126a and 126b indicate some possible locations of the spatial filter 126 to modulate the emanating light and/or to modulate the excitation light. For example, the spatial filter may be arranged within the flow channel, outside the flow channel, on a confining member of the flow channel, or may be arranged in any location relative to the objects to cause light emanating therefrom to be modulated. In some configurations, indicated by arrow 126a, the spatial filter 126 can be arranged between the flow channel 123 and the detector 130. In this position, the spatial filter 126 is referred to as an output spatial filter. In other configurations, indicated by arrow 126b, the spatial filter 126 can be arranged between the light source 112 and the flow channel 123. In this position, the spatial filter 126 is referred to as an input spatial filter. An input spatial filter may be adapted to transmit light emitted by the light source by varying amounts along the excitation region 123a of the flow channel 123. In this configuration, the input spatial filter creates patterned excitation light in the excitation region 123a of the flow channel 123.

According to various implementations, an input spatial filter may comprise a physical mask including a sequence or pattern of first mask features that have a first light transmission characteristic, e.g., are more light transmissive, and second mask features that have a second light transmission characteristic, e.g., are less light transmissive. The input spatial filter may alternatively or additionally comprise micro-optics or a patterned light source configured to create the excitation pattern. The excitation pattern can be imaged and/or directed onto the excitation region 123a using optical components for the imaging (e.g., lenses) and/or direction, (e.g., fiber optics or waveguides). In some embodiments an output spatial filter may be utilized and arranged between the objects 105 and the detector 130 at a detection region 123b of the flow channel.

In some embodiments, the excitation region 123a and the detection region 123b overlap. In other embodiments, there may be partial overlap between the excitation and detection regions or the excitation and detection regions may be non-overlapping or multiple detection regions and/or excitation regions may be used with various overlapping and/or non-overlapping arrangements.

In the assembly 100 shown in FIG. 1, the output spatial filter may be adapted to interact with the light 107 emanating from the objects 105 in the flow channel 123. In some embodiments, the output spatial filter may be a physical mask comprising a sequence or pattern of first mask features that are more light transmissive and second mask features that are less light transmissive. In some embodiments, color spatial filters may be used such that first mask features of the color spatial filter have a first light wavelength band pass characteristic and second mask features that have a second light wavelength band pass characteristic. The first and second light wavelength band pass characteristics may be non-overlapping or partially overlapping in the wavelength range. For example, first light wavelength band pass characteristic may be passing green light and second light wavelength band pass characteristic may be passing red light.

According to some embodiments of the assembly 100 that include an input spatial filter, as an object 105 travels in the flow direction 123c in the excitation region 123a of the flow channel 123, light emanating from the light source 112 is alternately substantially transmitted to the object 105 and substantially blocked or partially blocked from reaching the object 105 as the object 105 travels along the flow direction 123c. The alternate transmission and non-transmission (or reduced transmission) of the excitation light 112a along the flow direction 123c produces time-varying light 107 emanating from the object 105. The time-varying light 107 emanating from the object 105 falls on the detector 130 and, in response, the detector 130 generates a time-varying detector output signal 134.

According to some embodiments of the assembly 100 that include the output spatial filter configuration, light 112a from the light source 112 illuminates the object 105, causing the object 105 to emanate light 107. As the object 105 travels in the flow direction 123c in the detection region 123b of the flow channel 123, the output spatial filter alternatively entirely or substantially blocks the light 107 emanating from the object 105 from reaching the detector 130 and substantially transmits the light 107 emanating from the object 105 to the detector 130. The alternate substantial transmission and blocking (or partial blocking) of the light 107 emanating from the object 105 as the object 105 flows through the detection region 123b produces time varying light that falls on the detector 130. In response, the detector 130 generates the time-varying detector output signal 134.

In some embodiments such as the embodiment of FIG. 1, the analyzer 150 may include a signal transform processor 140 that converts the time-varying detector output signal 134 to a frequency domain output signal 136 so as to provide spectral power as a function of frequency. The signal transform processor 140 is shown as part of the analyzer 150 in this embodiment, but may be part of the detector in some embodiments or may comprise separate circuitry in other embodiments. For example, in some embodiments, the signal transform processor 140 may be part of the analyzer circuitry along with the detector.

For conversion, the signal processor 140 may use known techniques such as discrete Fourier transform including, for example, a Fast Fourier Transform "FFT" algorithm. Thus, the frequency domain output signal 136 represents the frequency component magnitude of the time-varying detector output signal 134, where the frequency component magnitude is the amount of a given frequency component that is present in the time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of the time-varying signal 134. However, other methods or techniques of representing the frequency component magnitude, or other measures of the frequency component magnitude, may also be used. Examples may include e.g. the square root of the Fourier signal power, or the signal strength (e.g. as measured in voltage or current) obtained from a filter that receives as input the time-varying detector output signal 134.

In FIG. 1, the time-varying detector output signal and/or frequency domain signal are analyzed by analyzer 150. The analyzer 150 is configured to receive the time-varying detector output signal and/or frequency domain signal and to determine length of the object and/or other object characteristics, such as object velocity, based upon the time-varying detector output signal and/or frequency domain signal. As will be discussed subsequently, the various embodiments discussed herein provide examples of techniques for determining the length dimension of the object 105 using various mask designs and processing techniques. As used herein, the length of the object 105 is a dimension of the object 105 as measured in a direction substantially along a flow direction 123c of the flow channel 123, e.g., along the x-direction of the Cartesian coordinate system of FIG. 1.

Figure 2:
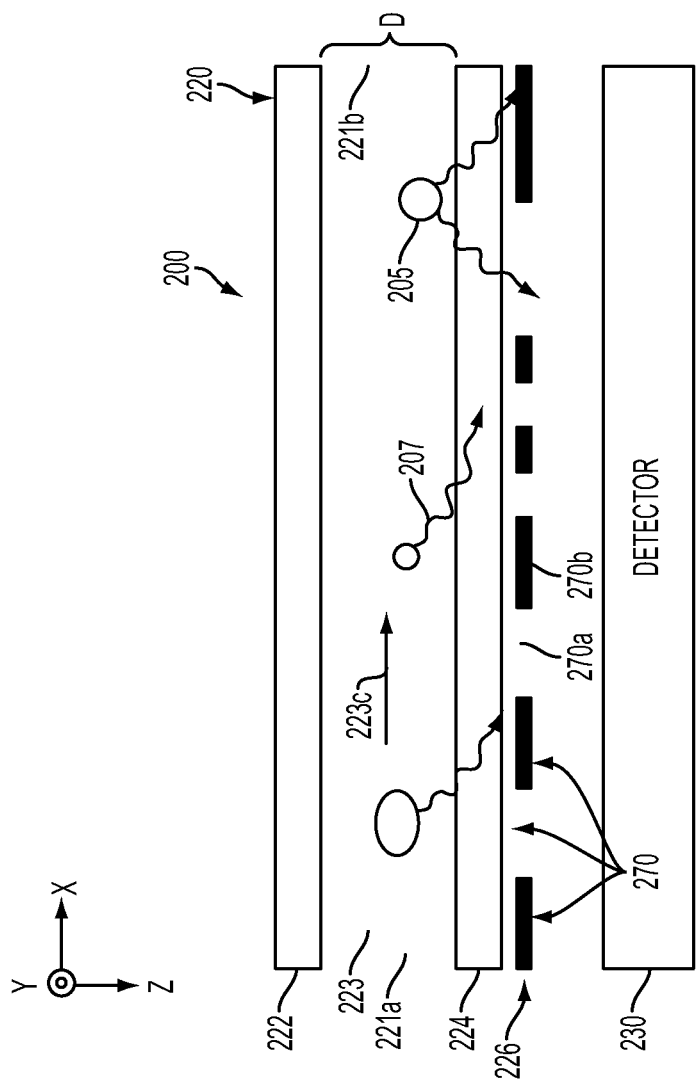
FIG. 2 is a side cross sectional view of another example embodiment of an assembly with the spatial filter positioned between the object and the detector.

FIG. 2 is an enlarged schematic view of a portion of an assembly 200 according to another example embodiment. The portion of the assembly 200 illustrated in FIG. 2A includes a flow path, e.g., fluidic device 220, a detector 230, and a spatial filter 226. The device 220 is adapted to receive a sample of interest to be analyzed. The sample may enter the device 220 at an inlet 221a thereof and exit the device 220 at an outlet 221b thereof, flowing generally in a flow direction 223c along the x-direction through a flow channel 223 formed between confining members 222, 224. As illustrated in FIG. 2, at least one object 205 can be disposed at a location within the flow channel 223. One or more objects in the flow channel 223 can have different lengths as measured in the x-direction of the Cartesian coordinate system illustrated. The objects 205 can have different widths in the y-direction of the Cartesian coordinate system and/or can have different thicknesses in the z-direction of the Cartesian coordinate system.

As discussed previously, the spatial filter 226 may comprise, for example, a spatial mask. As will be discussed in greater detail subsequently, the spatial filter 226 may have a plurality of mask features 270. The mask features 270 can include first features having a first light transmissive characteristic and second features having a second light transmissive characteristic, different from the first characteristic. For example, the first features 270a may be regions that are more light transmissive and the second features 270b may be regions that are less light transmissive. The pattern or sequence of transmissive features 270a and less transmissive regions 270b define a light transmission function that changes based on the characteristics of the object. This transmission function may be substantially periodic, or it may instead be substantially non-periodic. The light emanating from an object is sensed by the detector 230, which is configured to generate a time-varying output signal in response to the sensed light as previously discussed in connection with FIG. 1.

The spatial filter 226 may be substantially monochromatic or polychromatic as desired. In a monochromatic mask, the transmissive regions 270a all have substantially the same transmission characteristic, and the non-transmissive regions 270b also all have substantially the same transmission characteristic (but different from that of the transmissive regions 270a). In a simple case, the transmissive regions 270a may all be clear, as in the case of an aperture, and the less transmissive regions 270b may be opaque, as in the case of a layer of black ink, light blocking layer, or other absorptive, reflective, or scattering material. Alternatively, the transmissive regions 270a may all have a given color or light wavelength band pass characteristic, e.g., high transmission for light emanating from an excited object, but low transmission for excitation light. Alternatively, the less transmissive regions 270b may have a low but non-zero light transmission, as in the case of a grey ink or coating, or a partial absorber or reflector. In some embodiments, the spatial filter may include mask features that are opaque or less light transmissive alternating with first mask features that have a first light wavelength band pass characteristic in a first portion of the mask and mask features that are opaque or less light transmissive alternating with second mask features that have a second light wavelength band pass characteristic in a second portion of the mask.

In the embodiment of FIG. 2, the spatial filter 226 is positioned between the objects 205 and the detector 230 and between confining member 224 and the detector. The light emanating 207 from the objects 205 interacts with the spatial filter 226 to provide modulation of the light that falls on the detector 230. In some embodiments, the spatial filter may be positioned proximate to or within the flow channel.

Figure 3:
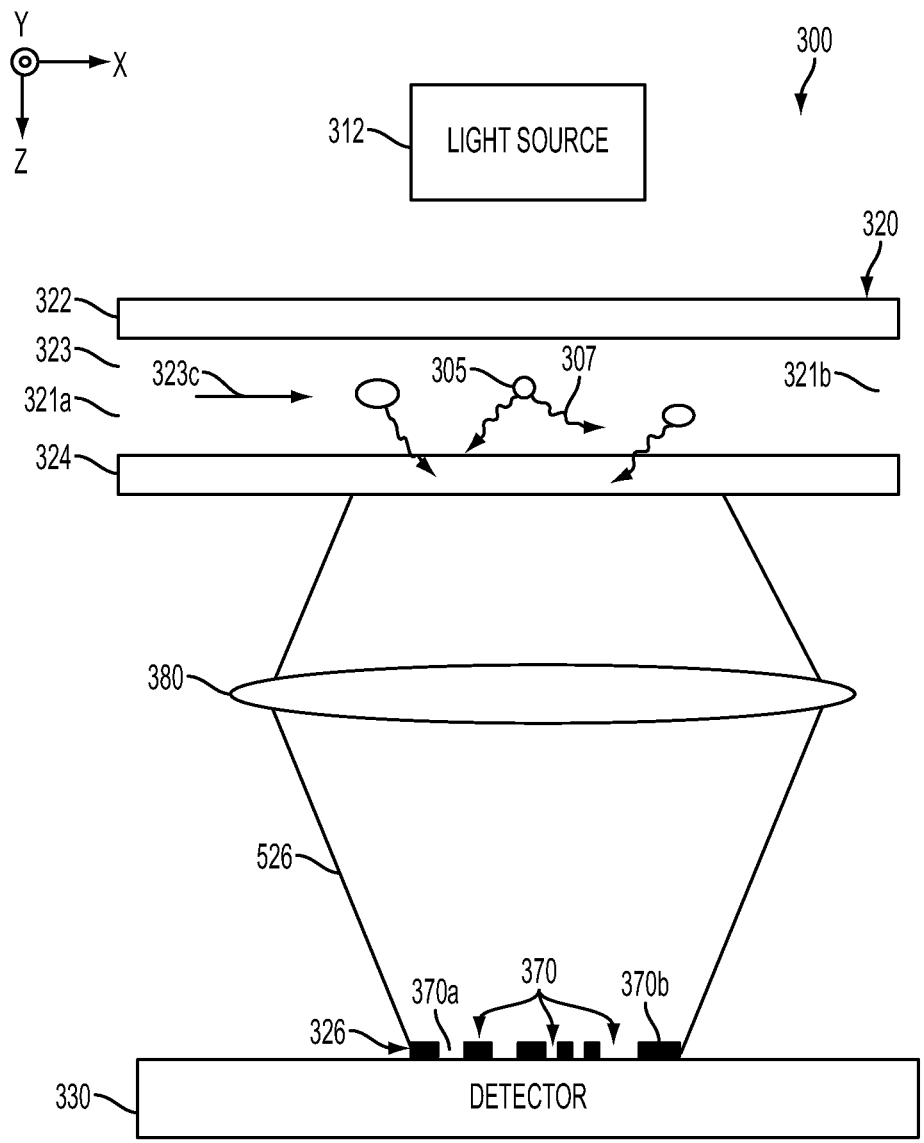
FIG. 3 is a schematic view of another example embodiment of an assembly with an optical imaging element positioned between the object and detector and the spatial filter positioned adjacent the detector.

FIG. 3 is a schematic view of another embodiment of a portion of an assembly 300 according to another example. The portion of the assembly 300 illustrated includes a light source 312, a spatial filter 326, a flow path, e.g., fluidic device 320, and a detector 330. Similar to the embodiments of FIGS. 1, and 2, the device 320 includes an inlet 321a, an outlet 321b, a flow channel 323 having a flow direction 323c, and confining members 322, 324. The spatial filter 326 includes mask features 370 including first mask features 370a having a first light transmissive characteristic and second mask features 370b having a second light transmissive characteristic. In FIG. 3, the spatial filter 326 is positioned between the objects 305 and the detector 330 and is positioned remotely from the flow channel 323 immediately adjacent the detector 330. An optical imaging element 380 such as a lens is positioned between the objects 305 and the filter 326 and is configured to image light from the objects 305 onto the spatial filter 326. The light emanating from the objects 305 and imaged by the element 380 interacts with the spatial filter 326 to provide modulation of the light sensed by the detector 330.

Figure 4:
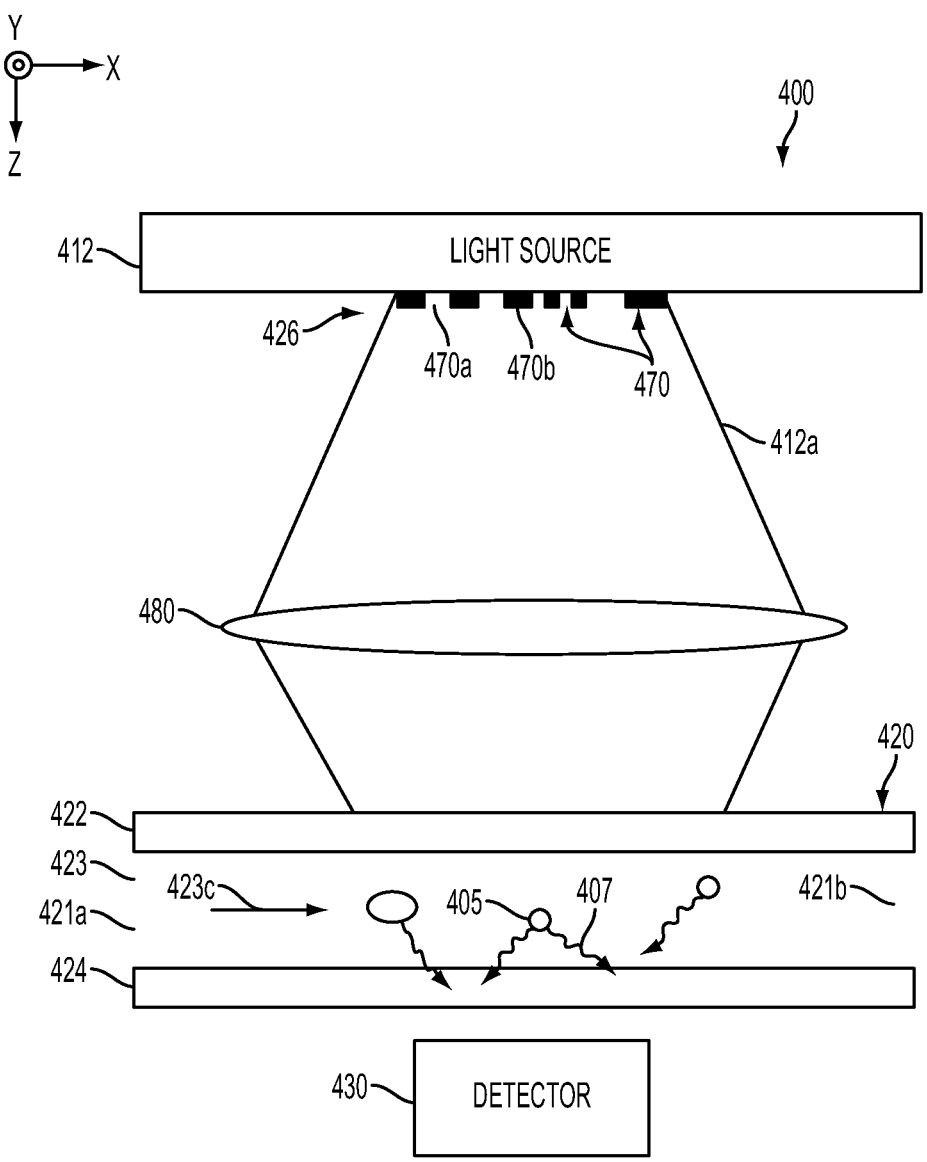
FIG. 4 is a schematic view of another example embodiment of an assembly with the optical imaging element positioned between the light source and the detector and the spatial filter positioned adjacent the light source.

FIG. 4 is a schematic view of yet another embodiment of a portion of an assembly 400. The portion of the assembly 400 illustrated includes a light source 412, a spatial filter 426, a flow path, e.g., fluidic device 420, and a detector 430. Similar to the previously discussed embodiments, the device 420 includes an inlet 421a, an outlet 421b, a flow channel 423 having a flow direction 423c, and confining members 422, 424. The spatial filter 426 includes mask features 470 such as first features that are light transmissive features 470a and second features that are less transmissive regions 470b. In FIG. 4, the spatial filter 426 is positioned between the light source 412 and the fluidic device 420 containing the objects 405. As shown, the spatial filter 426 is positioned remotely from the flow channel 423 immediately adjacent the light source 412. Interaction between the output light from the light source 412 and the spatial filter 426 causes spatially modulated excitation light 412a. An optical imaging element 480 is positioned between the filter 426 and the objects 405 and is configured to image the spatially modulated excitation light 412a onto an excitation region of the flow channel 423. Additionally, the optical imaging element 480 may incorporate one or more filters to narrow or otherwise tailor the spectrum of the resultant spatially modulated excitation light. The spatially modulated excitation light causes light 407 emanating from the objects 405 to be spatially modulated as well. The spatially modulated light emanating from the objects 405 is sensed by the detector 430.

Figure 5A:
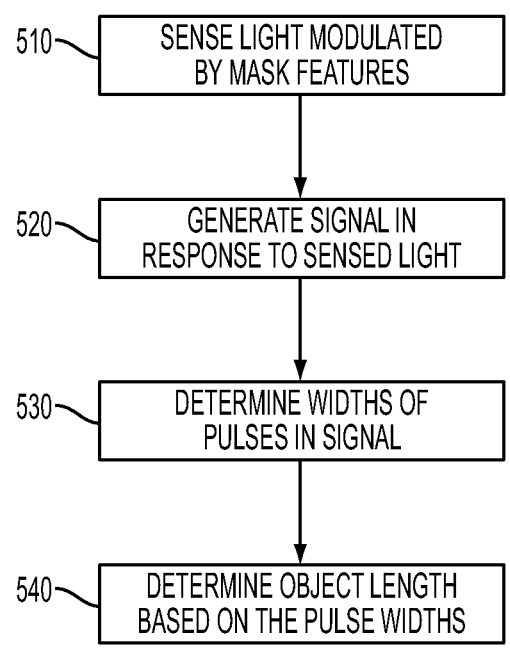
FIG. 5A is a flow diagram of a process for determining object length based on spatial modulation of light in accordance with some embodiments.

Embodiments discussed herein involve analytical approaches to determine various characteristics of objects in the flow path, such as the velocity of the objects and the length of objects along the flow direction of the flow path. FIG. 5A is a flow diagram illustrating a process of length determination in accordance with some embodiments. The approaches illustrated by FIG. 5A involve sensing 510 light emanating from at least one object moving in a flow path along a flow direction of a spatial filter. The spatial filter includes a plurality of mask features comprising first features alternating with second features along the flow direction, the first features having first light-transmission characteristics and the second features having second light transmission characteristics, different from the first light transmission characteristics. An intensity of the sensed light is modulated according to the mask features. A time varying electrical signal is generated 520 in response to the sensed light. The electrical signal includes a sequence of time modulated pulses associated with the mask features. A pulse width of at least some of the pulses is measured 530 at a predetermined fraction of the maximum amplitude of the pulses. The length of the object along the flow direction is determined 540 based on the measured pulse widths.

As an example, if the first mask features are substantially transparent and the second mask features are substantially opaque, the electrical signal comprises a sequence of pulses of one polarity, e.g., positive going pulses caused by the increase in light intensity corresponding to the clear features, alternating opposite polarity pulses, e.g., negative going pulses caused by the decrease in light intensity that decrease in amplitude at least partially corresponding to the opaque features. The width of the positive going pulses, the negative going pulses, or both, may be measured and used for object length determination.

Figure 5B:
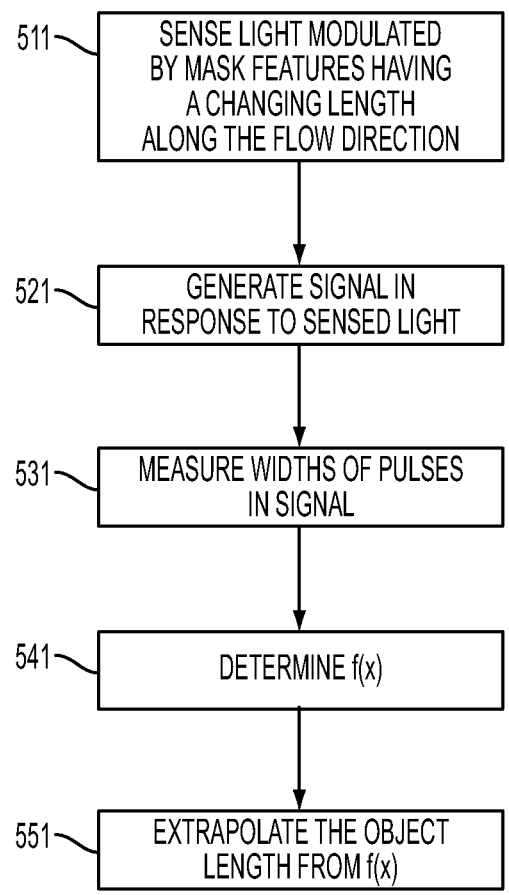
FIG. 5B is a flow diagram of a process for determining object length based on spatial modulation of light using a spatial filter having mask features that change in length along the flow direction in accordance with some embodiments.

As illustrated by the flow diagram of FIG. 5B, in some embodiments the length of the first and/or second mask features changes along the flow direction of the spatial filter. For example, the mask feature length may change linearly, logarithmically, randomly, or according to any pattern. The sensed light is modulated by the mask features having the changing length. The detector senses 511 the modulated light and generates 521 an electrical signal in response to the sensed light. The electrical signal includes a sequence of positive going pulses caused by the increase in light intensity, alternating with negative going pulses caused by the decrease in light intensity. The pulse widths of at least some of the pulses are measured 531. For example, in some embodiments the pulse widths of one polarity, e.g., positive pulse widths, are measured at a fraction of the maximum amplitude of the pulses. The length the object along the flow path is determined. Object length determination is based on the measured pulse widths and involves identifying 541 a function, f(x) that fits the data set ($x_i,y_i$), where each $x_i$ is associated with an $i^{th}$ mask feature and each $y_i$ is associated with an $i^{th}$ measured pulse width corresponding to the $i^{th}$ mask feature. The object length is determined 551 by extrapolation of the function f(x). In some cases, the function may be a linear function, the slope and intercept of which fitted from the measured data set using a least-square linear fit model, for example. In other cases, the function may be a logarithmic or an exponential function. Pulse width measurement outliers may be eliminated using a statistical technique such as random sample consensus (RANSAC).

In some spatial filter configurations, the first mask features are clear (or more light transmissive to the light interacting with the first mask features) and the second mask features are opaque (or less light transmissive to the light interacting with the second mask features). Extrapolation of the object length can involve determining the value of f(x) when a feature length of the first mask features is mathematically set to zero. In some implementations, the first light transmission characteristic corresponds to a particular color of light and determining the length of the object involves determining the length of an object having the particular color.

Figure 5C:
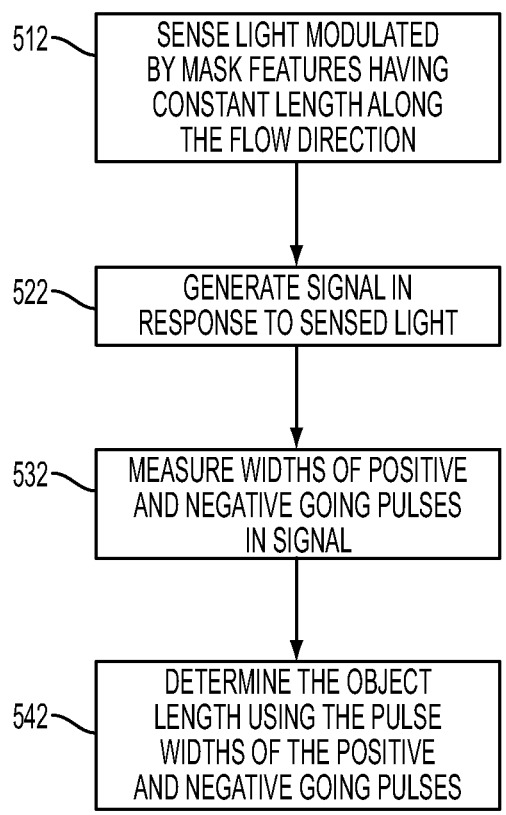
FIG. 5C is a flow diagram of a process for determining object length based on spatial modulation of light using a spatial filter having mask features that are constant in length along the flow direction in accordance with some embodiments.

FIG. 5C illustrates another embodiment wherein the feature length of the first and second mask features is constant along the flow direction of the spatial filter. In some cases the length of the first features is substantially equal to the length of the second features. Light emanating from the objects is sensed 512 and an electrical signal is generated 522 in response to the sensed light. For length determination, the pulse widths are measured 532 at a fraction of the maximum amplitude other than 50% (half maximum). At 50% of the maximum amplitude, the pulse width is substantially independent of object length. For example, the pulse widths of the positive and/or negative going pulses can be measured 532 at a fraction, e.g., 20% of the maximum amplitude of the pulses, or in a range of about 10% to about 40% or in a range of about 60% to about 90% of the maximum amplitude of the pulses. It is generally more difficult to accurately measure a pulse width at a very small and/or very large fraction of the maximum amplitude due to the presence of noise. Hence the operational measurement range typically excludes the regions of extreme fraction values, as well as the region near 50% of maximum amplitude where the pulse width is substantially independent of the object length.

In some implementations, the velocity of the objects can be determined by measuring the pulse width at 50% of the maximum amplitude and calculating an average of the positive and negative going pulse widths in the pulse pairs. The velocity of the object is related to the slope of the averages with respect to a pulse (or mask feature) number.

Optionally, analysis of the pulse widths of the positive and negative going pulses can be used to determine whether objects are slowing down or accelerating as they move in the flow path past the spatial filter as discussed below in conjunction with FIGS. 15A-15B. Optionally, analysis of the pulse widths of the positive and negative going pulses can be used to identify whether multiple objects are traveling together along the flow path and/or to determine the distance between the multiple objects as discussed below in conjunction with FIGS. 16-19. In some implementations, identification of multiple objects traveling in the flow path and/or determining the distance between multiple objects in the flow path involves analysis of the modulation envelope of the positive and negative going pulses. In some implementations, the length of the objects can be determined at least in part by the rise times and/or fall times of the pulses. For mask features that have a length along the flow direction equal to or greater than the length of the objects, the pulses reach their maximum value when the object is fully exposed in the mask feature. For objects traveling at about the same velocity, shorter objects produce pulses that have a shorter rise time than longer objects.

Figure 6A:
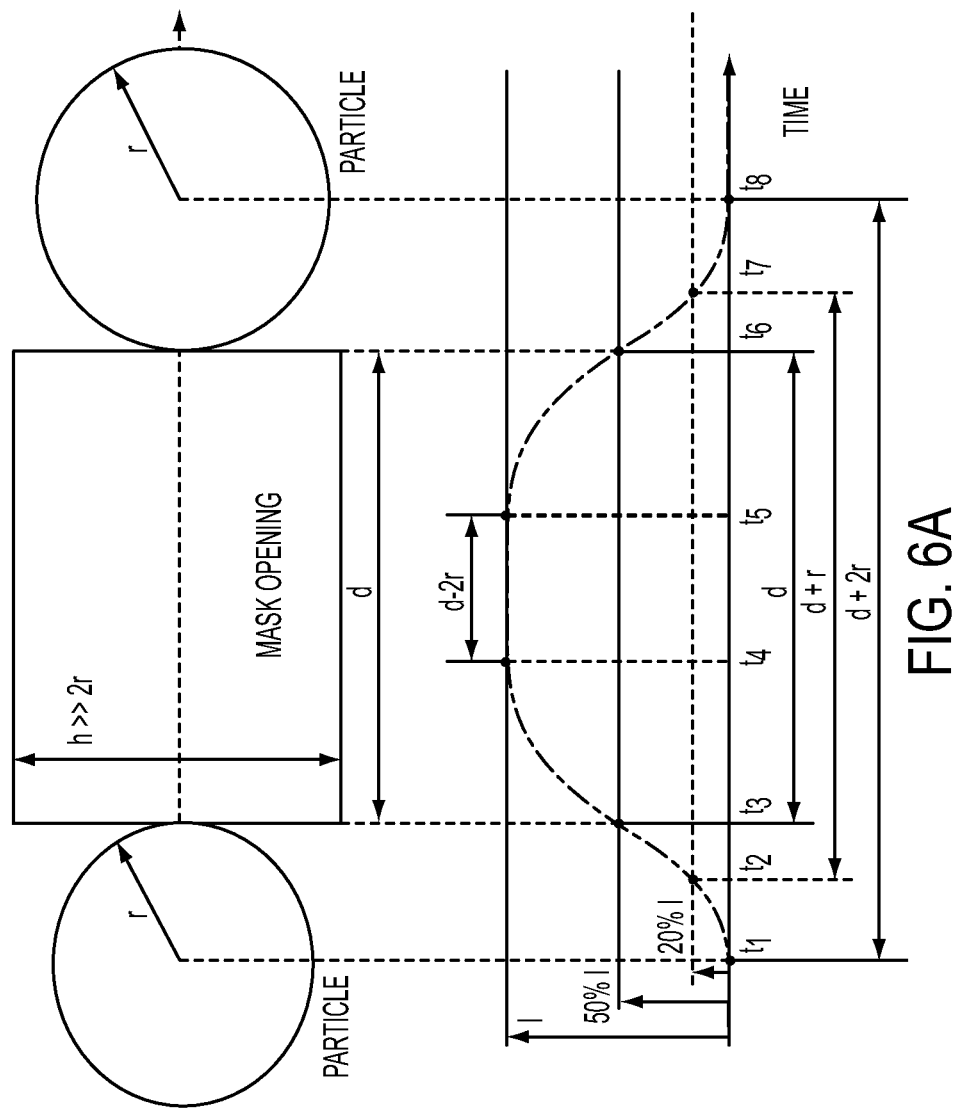
FIG. 6A provides an idealized graph of light emanating from an object having a circular cross section along the flow direction as the object traverses a light transmissive mask feature.

The upper portion of FIG. 6A illustrates an object having a circular cross section of radius r that traverses a mask feature of length d and height $>>2r$. The lower portion of FIG. 6A is an idealized graph of the intensity of light emanating from the object as it traverses the mask feature. The object of radius r is shown at two moments in time: at time $t_1$, immediately before the object begins its traverse across the mask feature, and at time $t_8$, immediately after the object has completed its traverse across the mask feature. At both of these times, $t_1$ and $t_8$, light emanating from the object is 0 in the idealized intensity graph, since the entire object is fully outside of the mask feature. At times $t_2$ and $t_7$, the light emanating from the object is 20% of the maximum intensity, I. At times $t_3$ and $t_6$, the object is half within and half out of the mask feature and the light emanating from the object is 50% of the maximum intensity, I. Between times $t_4$ and $t_5$, the object is fully exposed in the mask feature and the intensity of the emanating light is at the maximum intensity, I. Note that although the object is illustrated as having a circular cross-section, the object may have any shape or length along the flow direction. For example, the object may have an elliptical or oval cross section with the long axis of the ellipse or oval lying along the flow direction. The analysis illustrated by FIG. 6A can be applied for objects having any cross sectional shape along the flow direction, e.g., oval or elliptical.

For an object traveling at known, constant velocity, v, and a known mask feature length, d, the length of the object can be determined from the intensity pulse width at some fraction of the maximum amplitude. However, it will be appreciated that according to the analysis of FIG. 6A, the pulse width at 50% intensity is equal to the mask feature length independent of the object length so long as the mask feature length is at least equal to the object length (object length=2r in this example). The pulse width (in seconds) at 20% of maximum intensity is equal to $t_7-t_2$; the pulse width (in µm) at 20% of maximum intensity is equal to $(t_7-t_2) \cdot v = d+r$. The pulse width (in seconds) at maximum intensity is equal to $t_5-t_4$; the pulse width (in µm) at maximum intensity is equal to $(t_5-t_4) \cdot v = d-2r$.

Figure 6B:
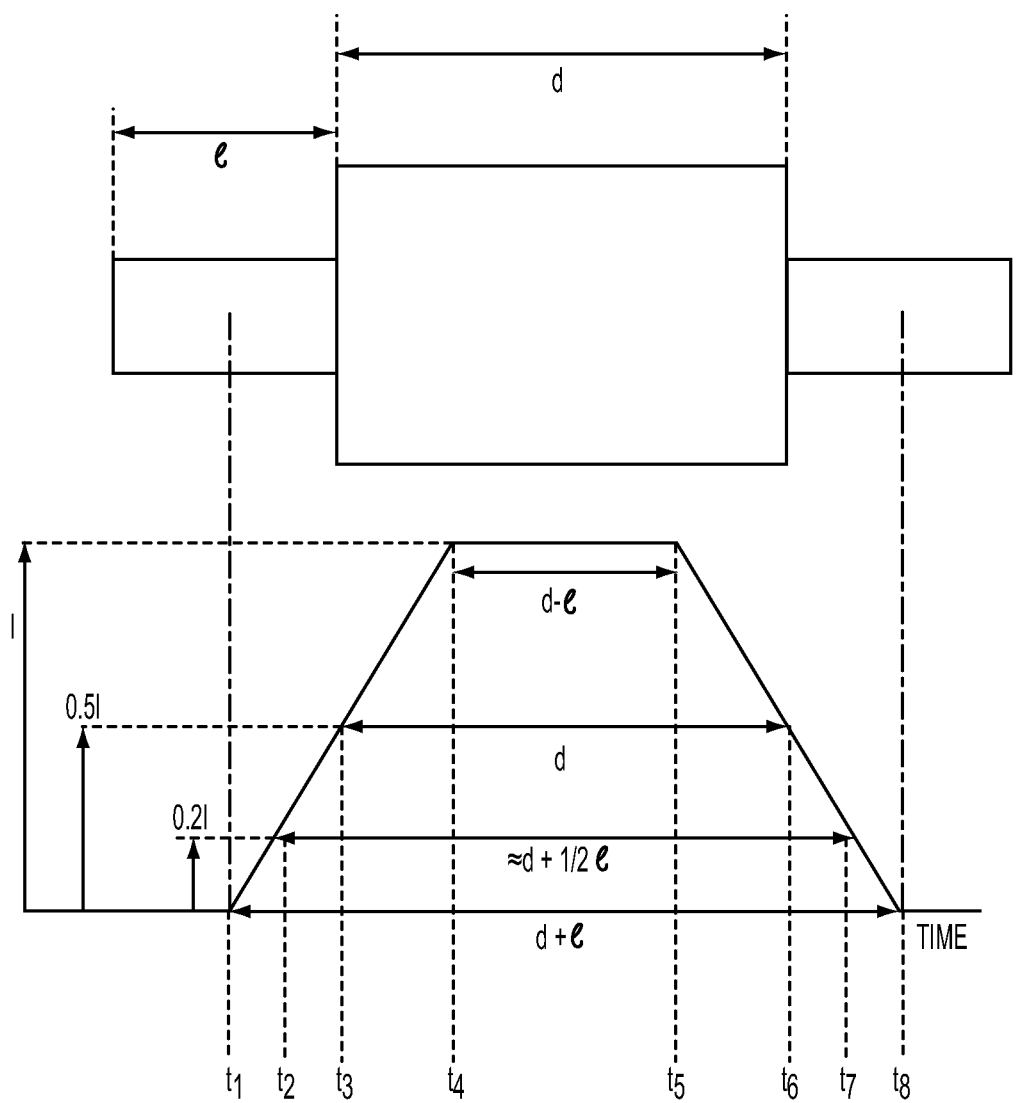
FIG. 6B provides an idealized graph of light emanating from an object having a rectangular cross section along the flow direction as the object traverses a light transmissive mask feature.

FIG. 6B is another example of the intensity profile of light emanating from an object as it traverses a mask feature. The upper portion of FIG. 6B illustrates an object of length l, and a mask feature of length d and height $>>2r$. The lower portion of FIG. 6B is an idealized graph of the intensity of light emanating from the object as it traverses the mask feature. The object is shown at two moments in time: at time $t_1$, immediately before the object begins its traverse across the mask feature, and at time $t_8$, immediately after the object has completed its traverse across the mask feature. At both of these times, $t_1$ and $t_8$, light emanating from the object is 0 in the idealized intensity graph, since the entire object is fully outside of the mask feature. At times $t_2$ and $t_7$, the light emanating from the object is 20% of the maximum intensity, I. At times $t_3$ and $t_6$, the object is half within and half out of the mask feature and the light emanating from the object is 50% of the maximum intensity, I. Between times $t_4$ and $t_5$, the object is fully exposed in the mask feature and the intensity of the emanating light is at the maximum intensity, I.

For an object traveling at known, constant velocity, v, and a known mask feature length, d, the length of the object can be determined from the intensity pulse width at some fractions of the maximum amplitude. However, it will be appreciated that according to the analysis of FIG. 6B, the pulse width at 50% intensity is equal to the mask feature length independent of the object length so long as the mask feature length is at least equal to the object length (object length=l in this example). The pulse width (in seconds) at 20% of maximum intensity is equal to $t_7-t_2$; the pulse width (in µm) at 20% of maximum intensity is equal to $(t_7-t_2) \cdot v \approx d+1/2 \, l$. The pulse width (in seconds) at maximum intensity is equal to $t_5-t_4$; the pulse width (in µm) at maximum intensity is equal to $(t_5-t_4) \cdot v = d-l$.

Figure 7:
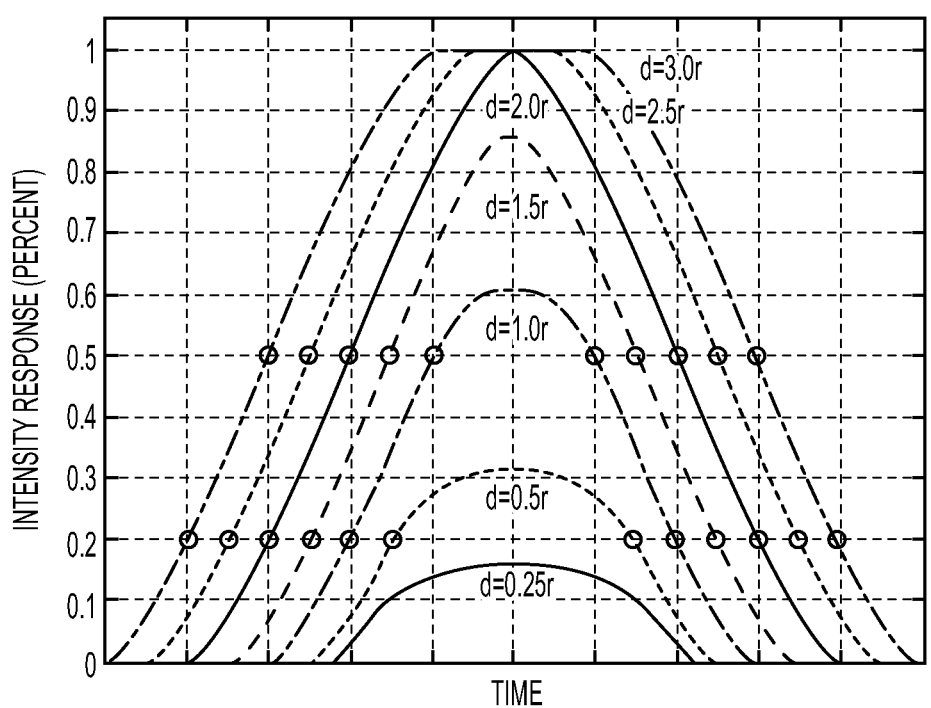
FIG. 7 shows a family of graphs of the intensity of emanating light for a number of mask feature lengths.

FIG. 7 shows a family of curves of the intensity of the light emanating from an object of circular cross section with radius r, wherein the object traverses mask features of length, d, where d is expressed as a function r. The family of curves indicates that where d is greater than or equal to the object length (d=2r in the case of a circular cross section area object), the pulse width (in µm) at 50% maximum is equal to the mask feature length. For d less than the object length, the maximum intensity decreases causing the pulse width at 50% maximum intensity to decrease. In this situation, the above relationship is no longer applicable.

In general, for length determination by linear curve fit and extrapolation, two or more mask first features (more light transmissive features) having differing lengths can be used. These mask features can be arranged in any order, but mask features with length that varies linearly along the flow direction, as depicted in FIG. 8A can make analysis more straightforward. FIG. 8A shows a perspective view of a portion of a fluidic device 820 and a spatial filter 826. The fluidic device 820 includes a flow channel 823 having a flow direction 823a and confining members 822, 824, 827, and 828. Although the confining members 822, 824, 827, and 828 are positioned to define the flow channel 823, in other embodiments one or all of the confining members 822, 824, 827, and 828 may not be used. The flow direction 823a aligns generally with the x-direction of the Cartesian coordinate system illustrated in FIG. 8A. In the embodiment shown, the spatial filter 826 is disposed proximate to confining member 822. In other embodiments, the spatial filter 826 may be disposed within the flow channel 823, mounted to any of the confining members 822, 824, 827, 828, positioned relative to any of the confining members 822, 824, 827, 828, positioned on or relative to the light source (not shown) or detector (not shown). The detector may be positioned in any appropriate location to sense light emanating from objects moving in the flow channel 823 that is modulated by filter 826.

Figure 8B:
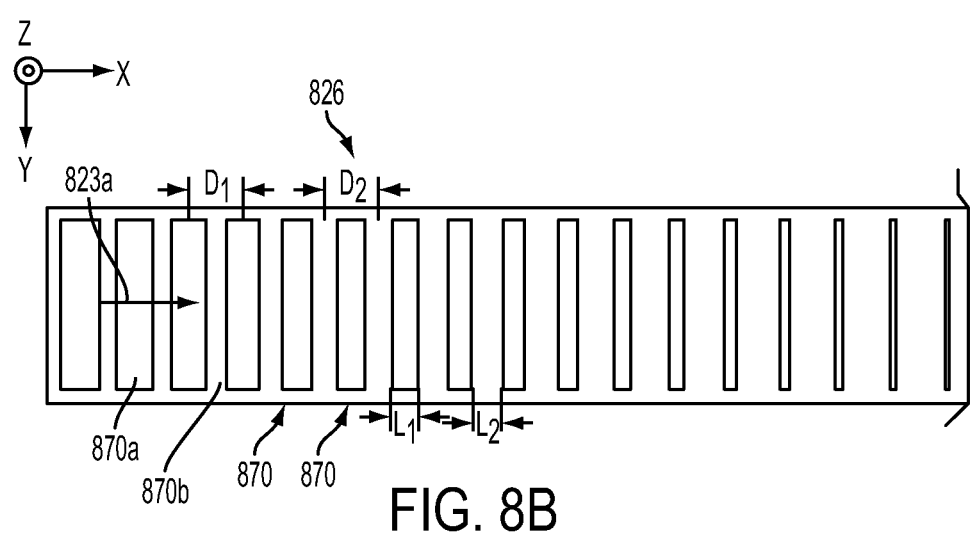
FIG. 8B shows the spatial filter of FIG. 8A in more detail.

In FIG. 8A, the spatial filter 826 is arranged in the x-y plane of the Cartesian coordinate system. The spatial filter 826 can have a plurality of mask features 870 arranged such that the modulated light from the object and the output electrical signal that results therefrom provides time modulated pulses from which the length of the objects passing through the flow channel 823 can be determined. The spatial filter 826 can have pattern of mask features such that a length of the features in the x direction changes linearly, as shown in the perspective view of FIG. 8A and the top view of FIG. 8B. The frequency (also referred to as pitch) of the mask features may be constant along the flow direction. The pitch used for the spatial filter depends on the length of the objects being measured. For example, in some configurations, the fixed pitch may be about 30 μm. In some embodiments the pitch value may be fixed for all mask features regardless of the mask feature length in order to provide robust detection, in the frequency domain, of the presence of an object in the channel, even when the amount of light emanating from the object is very dim. In other embodiments, the pitch value may be variable between the mask features.

In the exemplary embodiment shown in FIGS. 8A and 8B, the mask features 870 include first mask features 870a that have a first light transmission characteristic, e.g., are more light transmissive, alternating with second mask features 870b that have second light transmission characteristics, e.g. are less light-transmissive. The first light transmissive characteristics of the first mask features 870a are different from the second light transmissive characteristics of the second mask features 870b. As will be discussed subsequently, the length of the first mask features 870a and/or the length of the second mask features 870b can change along at least a portion of the spatial filter 826 in the flow direction of the flow channel 823 (the x-direction in FIGS. 8A and 8B). The length of a mask feature is measured along the flow direction (the x-direction in FIGS. 8A and 8B). In the exemplary embodiment of FIG. 8A, the length of the first mask features 870a linearly decreases along the flow direction 823a of the flow channel 823. The length of the second mask features 870b linearly increases along the flow direction 823a of the flow channel 823.

FIG. 8B is a plan view of spatial filter 826 of FIG. 8A. FIG. 8B illustrates the mask features 870 in greater detail. Mask features 870 include first mask features 870a alternating with second mask features 870b. In the embodiment shown, the first mask features 870a have a constant frequency and changing length along the x-direction. The constant frequency results from center-to-center distances $D_1$ in the x-direction that remain constant for each mask feature 870a. Thus, each of the first mask features 870a has a center that is spaced a same distance $D_1$ from the center of an adjacent first mask feature 870a. Similarly, each of the second mask features 870b has a center that is spaced a same distance $D_2$ from the center of an adjacent second mask feature 870b. In the embodiment of FIGS. 8A and 8B, $D_1$ is equal to $D_2$. Although the examples provided refer to first and second mask features having first and second light transmission characteristics, respectively, it will be appreciated that a spatial filter may include additional third, fourth, etc. mask features, wherein each of the first, second, third, fourth, etc. mask features have different light transmission characteristics.

The changing duty cycles of the first and second mask features 870a, 870b is the result of changing lengths $L_1$, $L_2$ along the x-direction. Thus, each of the first mask features 870a has a length $L_1$ measured from a first starting edge to a second trailing edge. The length $L_1$ of the first mask features 870a is a function of position along the flow direction 823a.

In the embodiment shown, mask features 870 are patterned in a desired manner with dimensions $D_1$ and $D_2$ being the same and $L_1$ and $L_2$ changing in a linear manner. However, in other embodiments mask features 870 may be patterned in another manner (e.g., quadratically, logarithmically, exponentially, inverse proportionally, and/or random) that allows for a data set of pulse widths from the output signal that are associated with lengths of mask features. Thus, the mask features of the spatial filter can be arranged in any order, so long as a data set comprising pulse widths as a function of mask feature length can be obtained for analysis.

Figure 9:
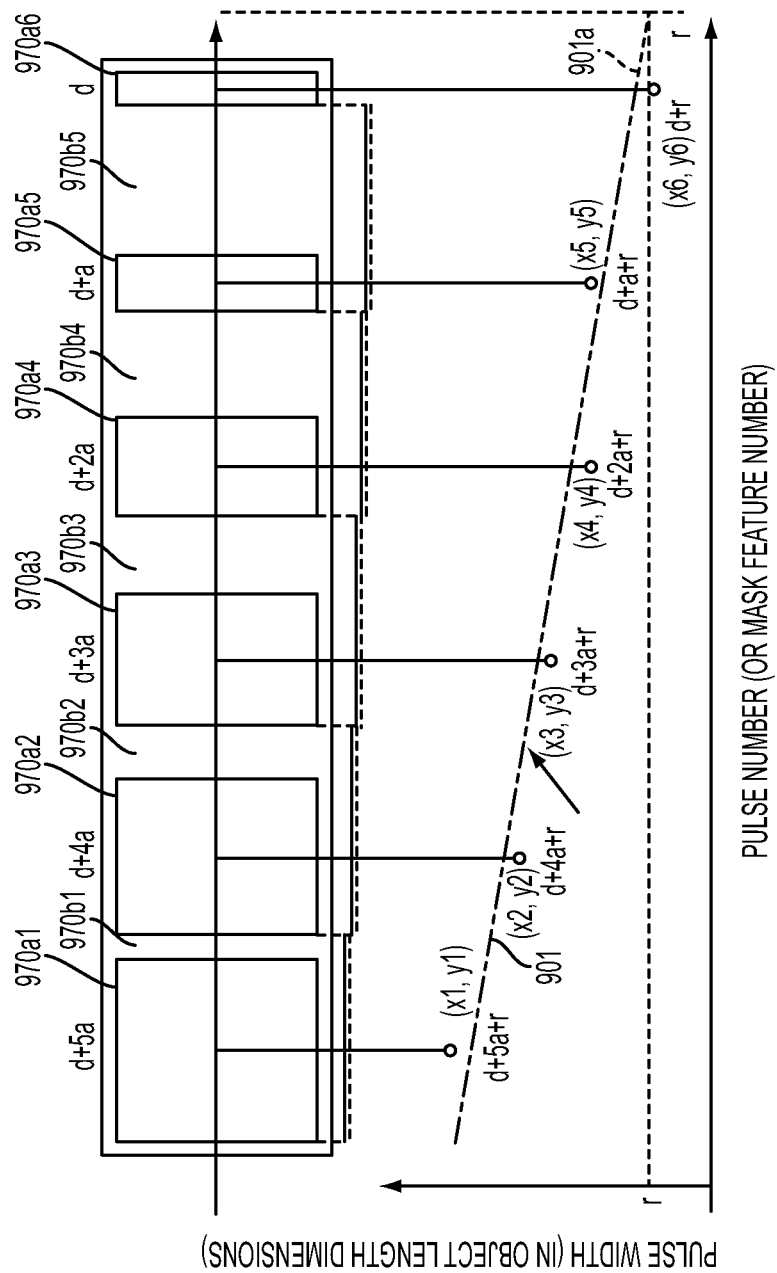
FIG. 9 illustrates a process for determining object length by extrapolating a function fitted to measured data in accordance with some embodiments.

FIG. 9 illustrates a process of determining the object length using a mask 970 with first mask features 970a1-970a6 that decrease linearly in length along the flow direction. The top portion of FIG. 9 shows six first mask features 970a1-970a6 that are more light transmissive alternating with five second mask features 970b1-970b5 that are less light transmissive. The length of the first mask features 970a1-970a6 decreases linearly along the flow direction (x-direction). Feature 970a1 has a length d+5a, where d is the length of the smallest first mask feature 970a6 and a is any constant. Feature 970a2 has length d+4a; feature 970a3 has length d+3a; feature 970a4 has length d+2a, feature 970a5 has length d+a, feature 970a6 has length d. In this embodiment, the pitch is constant throughout the mask, as can be seen by the distance between the centers of subsequent mask features of either the first or second mask features.

As an object moves relative to the spatial filter along the flow direction, the emanating light is sensed by the detector (not shown in FIG. 9) which generates time modulated pulses responsive to the sensed light. The pulses have pulse widths related to the mask feature lengths as previously described in connection with FIG. 6A. In one scenario, using 20% of maximum intensity, the pulse width (in units of length) of the pulse generated as the object traverses feature 970a1 is d+5a+r; the pulse width of the pulse generated as the object traverses feature 970a2 is d+4a+r; the pulse width of the pulse generated as the object traverses feature 970a3 is d+3a+r; the pulse width of the pulse generated as the object traverses feature 970a4 is d+2a+r; the pulse width of the pulse generated as the object traverses feature 970a5 is d+a+r; and the pulse width of the pulse generated as the object traverses feature 970a6 is d+r. It will be appreciated that the actual pulse widths will be measured in a range around these values due to measurement error and noise. The pulse width measurements provide a set of mask feature measurement points $\{p_i\}$, each point given by $p_i=(xi,yi)$, where each $x_i$ is the $i^{th}$ mask feature length and each $y_i$ is the pulse width measurement, e.g., at 20% of the maximum value corresponding to the $i^{th}$ mask feature.

The set of mask feature length measurement points $\{p_i\}$ are conceptually shown as the set of circled points in FIG. 9. If the measurement errors are small, the set of points would ideally fall on the linear curve 901. In practice, however, each point may fall slightly above or below the curve in the y direction, due to measurement error and noise associated with the $i^{th}$ mask feature pulse width measurement. A function $f(\{p_i\},x)$ is determined that fits the set of points $\{p_i\}$, such as the line 901 shown in FIG. 9. The function $f(\{p_i\},x)$ predicting the expected pulse width measurement of an hypothesized mask feature of length x, based on all the given mask feature measurements $\{p_i\}$, for any value of x, not necessarily restricted to any one of existing feature lengths on the mask. For example, $f(\{p_i\},x)$ may be determined by a linear regression model, such as by using a least squares approach.

The function f(x) transforms the discrete set of pulse width measurement points at the given mask features lengths $\{p_i\}$ into a continuous function that virtually predicts the estimated pulse width for any mask feature length x, even if this feature length is not actually present as one of the existing mask features (i.e., the mask does not actually include a mask feature having this length). The function $f(\{p_i\},x)$ allows to extrapolate the predicted pulse width for any mask feature length x, and in particular, for an infinitely small x→0 feature length. Extrapolating the function by mathematically setting the mask feature length to zero effectively eliminates the mask feature length, regardless of its actual size, and yields the estimated radius of the object, where the length of the object is twice the estimated radius. The extrapolation projects the imaginary extension 901a of the fitted line f(x) 901 to the point where d=0 which is the virtual zero opening mask feature width. The length estimation provided by the extrapolation using this technique is self-calibrating, i.e., does not require a separate calibration process for each different mask, since the extrapolated function f(x) is no longer dependent on the actual length of the smallest mask feature size d. However, the absolute object length measurement is dependent of the velocity of the object which is assumed to be constant. The technique is well suited for measuring the object lengths of variable object sizes, small and large, which may be traveling at different velocities in the channel because there are several ways to measure the particle velocity.

Figure 10:
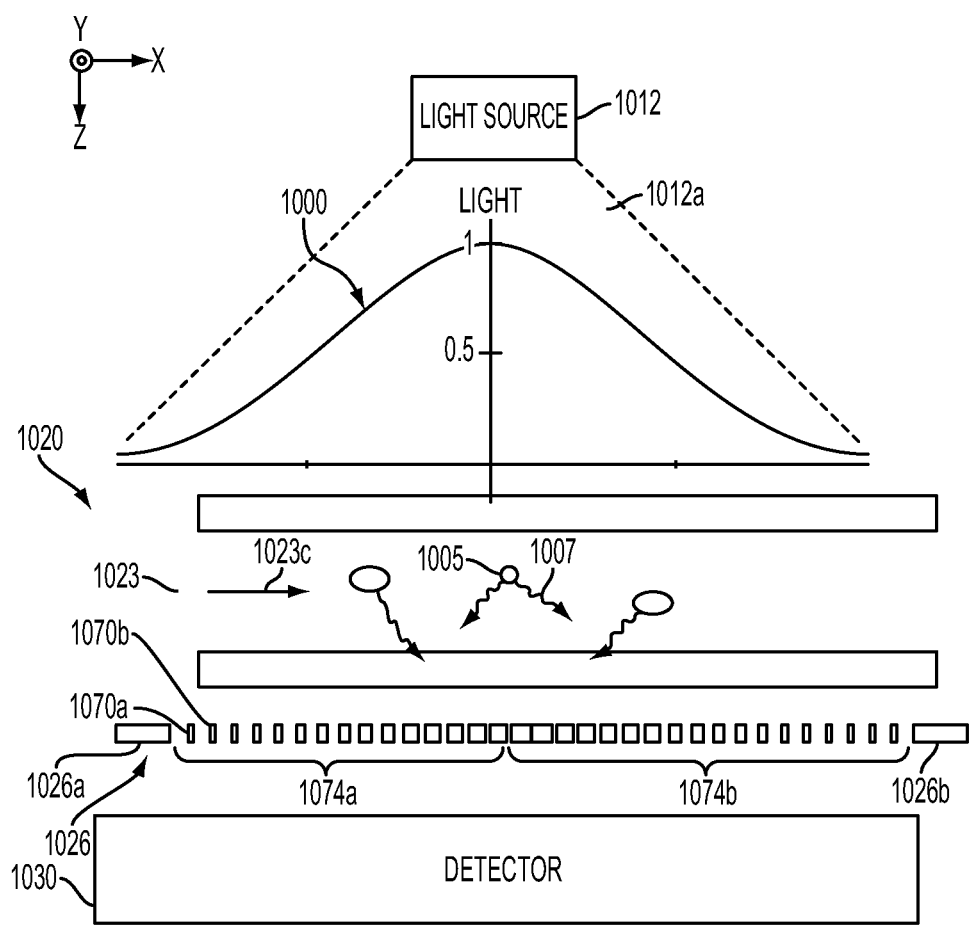
FIG. 10 illustrates a spatial modulation system that includes a spatial filter with first and second symmetrical portions containing mask features having a length that changes along the flow direction, the spatial filter used in conjunction with a light source with a Gaussian intensity distribution.

FIG. 10 shows a cross section of a spatial filter 1026 including the first half region 1074a and second half region 1074b arranged in relation to a light source 1012, fluidic device 1020, and a detector 1030. The spatial filter 1026 includes mask features including a number of first mask features 1070a that are more light transmissive and a number of second mask features 1070b that are less light transmissive. Objects 1005 move in the fluidic device 1020 along a flow direction 1023c and emanate light 1007. Although the objects 1005 are illustrated as having a length in the x direction greater than the lengths of the mask features 1070, it will be understood that the lengths of the objects 1005 may actually be smaller than at least some of the lengths of the mask features 1070. Furthermore, it will be understood that the speed of the objects 1005 is substantially constant. FIG. 10 shows an intensity distribution 1000 of light 1012a emitted from a light source 1012 and distributed along the flow channel 1023 of the fluidic device 1010. In the embodiment shown, the intensity distribution 1000 of the light 1012a is not uniformly distributed along the flow channel but rather has an approximately Gaussian distribution, with the strongest intensity at the center and tapering off to either side. However, in other embodiments the intensity distribution may vary from the example embodiment illustrated.

In a representative embodiment, the mask features are disposed in a first section arranged in a first linear chirp pattern and a second section arranged in a second linear chirp pattern, wherein the first pattern and the second pattern are symmetrical around a center line extending laterally across the spatial filter. The first mask features are substantially transparent and the second mask features are substantially opaque. The substantially transparent features have a length of about 1 μm at the center line of the mask. The clear features of the first pattern have a linear decrease in length of about 1.5 μm along the flow direction and the clear features of the second pattern have a linear increase in length of about 1.5 μm along the flow direction, while the pitch is constant throughout the mask at about 40 μm. It should be appreciated that the above dimensions are designed for detecting and measuring a specific range of object sizes traveling at a specific velocity range in the channel, and will generally vary based on the desired object size and velocity range.

Figure 11:
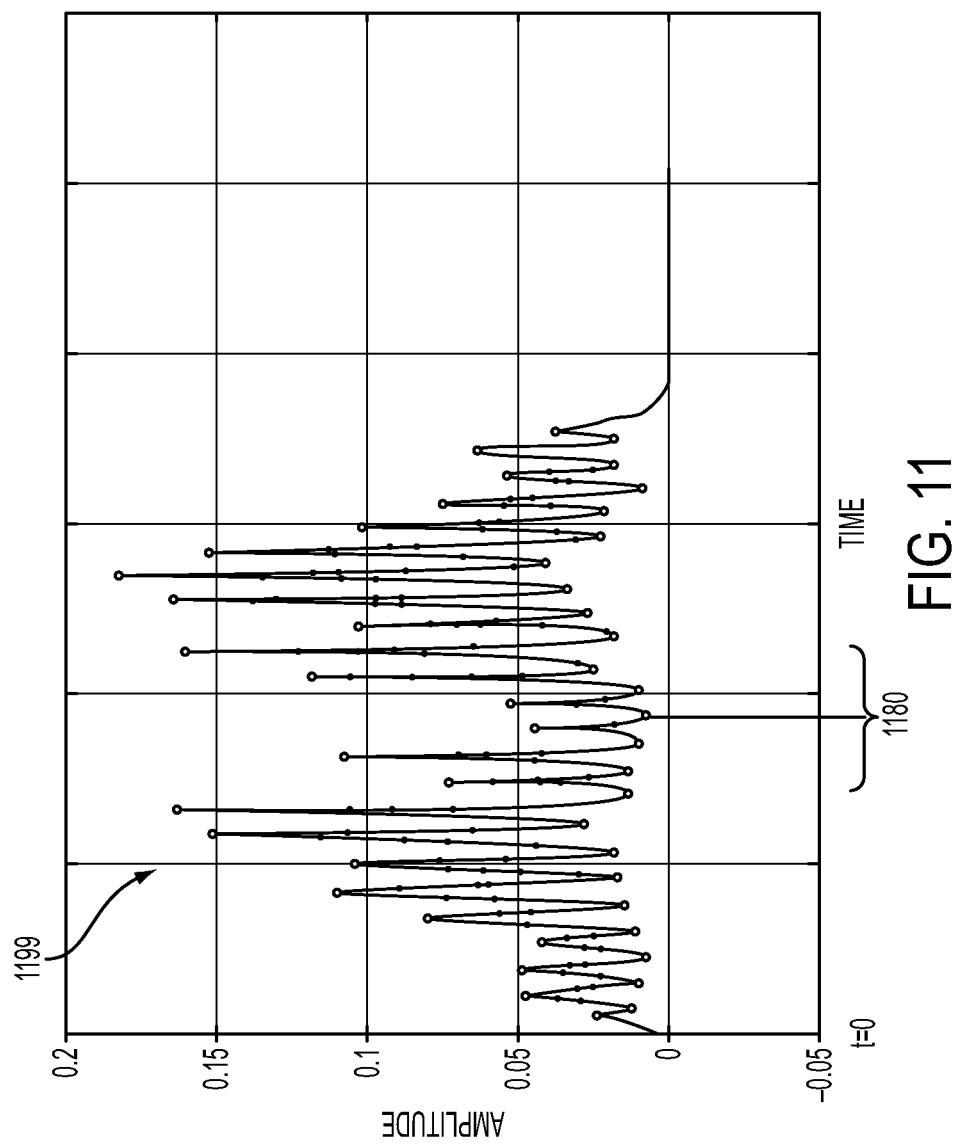
FIG. 11 is a graph of a signal generated by the detector of the system depicted in FIG. 10 as an object moves through the detection region.

FIG. 11 is a simplified plot of an electrical signal 1199 that is generated by detector 1030 in response to sensing the modulated light that has passed through the mask features of the spatial filter 1026 of FIG. 10. The morphology of the electrical signal 1199 generated by the detector 1030 results from the intensity distribution 1000 of the light output 1012a from the light source 1012 and the interaction of the light 1012a with the mask features 1070, and object specific characteristics. As shown in FIG. 11, the output electrical signal 1199 generated by the detector 1030 includes a first set of positive going pulses having a pulse widths (or duty cycle) that decrease with respect to time (corresponding to the first portion 1074a of mask 1070) and a second set of positive going pulses having pulse widths (or duty cycle) that increase with respect to time (corresponding to the second portion 1074b of mask 1070). The pulse widths are narrower at the mask center, and gradually grow wider toward either end of the mask, in accordance with the mask pattern 1074a and 1074b in FIG. 10. The pulse frequency in this example is constant and is associated with the constant pitch and the constant velocity of the object as it moves along the flow. The pulse widths are associated with the velocity and the length of the object.

As shown, the amplitude of the pulses in the output electrical signal 1199 is initially lower toward at time t=0 due to the distribution of the input light 1012a (as exhibited by intensity profile 1000, which has a lower intensity toward the edges 1026a, 1026b of the spatial filter 1026. The amplitude of the pulses increases for a time period due to the increase in the intensity of the input light 1012a (as illustrated by intensity profile 1000) before falling in region 1180 due to the decreased mask feature length of the more light-transmissive regions 1070a (FIG. 6A) in the center region of the spatial filter 1026 which corresponds to region 1180 of the electrical signal 1199. Due to the symmetry of the input light 1012a and the mask pattern 1074a and 1074b around the mask center, the electrical output signal is also roughly symmetric around the mask center. The amplitude of the output electrical signal 1199 initially increases in the time period after the region 1180 due to the gradual increase in the mask feature length of the more light-transmissive regions 1070a (FIG. 6). After increasing for a time period, the amplitude of the output electrical signal 1199 eventually decreases and finally becomes zero due to a decrease in intensity of light as shown by intensity profile 1000. The dual portion mask shown in FIG. 10 is particularly useful to increase signal to noise ratio (SNR) in the signal when a light source having a Gaussian distribution is used because the mask features are largest where the intensity of light is smallest and the mask features are smallest where the intensity of light is greatest.

In addition, a particularly dim object may not generate a substantial amount of emanating light to be detectable through the narrowest first mask features 1070a (FIG. 6), in which case the first one or more time modulated pulses at the center of the mask may be missing. The dual portion mask design is particularly useful for identifying missing pulse peaks at the center of the mask, based on the constant pitch. A missing pulse is readily recognized by a resulting wider time gap between successive pulses. If instead the narrow first mask features were to be placed at the ends of the mask, then it would be much more difficult to tell if any pulses may be missing, and how many.

An analyzer can be configured to receive the output electrical signal 1199, determine widths of the pulses, fit a function, e.g., a line, to the pulse widths with respect to the lengths of the mask features 1070, and extrapolate a length of the object in the flow channel from the line. For the symmetrical dual portion mask shown in FIG. 10, the measurement of the pulse widths reveals two data sets: ($x_i$, $y_{1i}$) and ($x_i$, $y_{2i}$) where $x_i$ corresponds to the mask feature lengths (or mask feature number) for the first portion of the mask and $y_{1i}$ corresponds to the measured pulse widths× object velocity (in µm) produced by interaction of light with the mask features of the first mask portion 1074a, and $y_{i2}$ corresponds to the pulse widths×object velocity (in µm) produced by interaction of light with the mask features of the second mask portion 1074b. Determining the length of the object can involve fitting f(x) to both data sets (x, $y_{1i}$), (x, $y_{2i}$) and extrapolating the object length as previously discussed in connection with FIG. 9.

Figure 12:
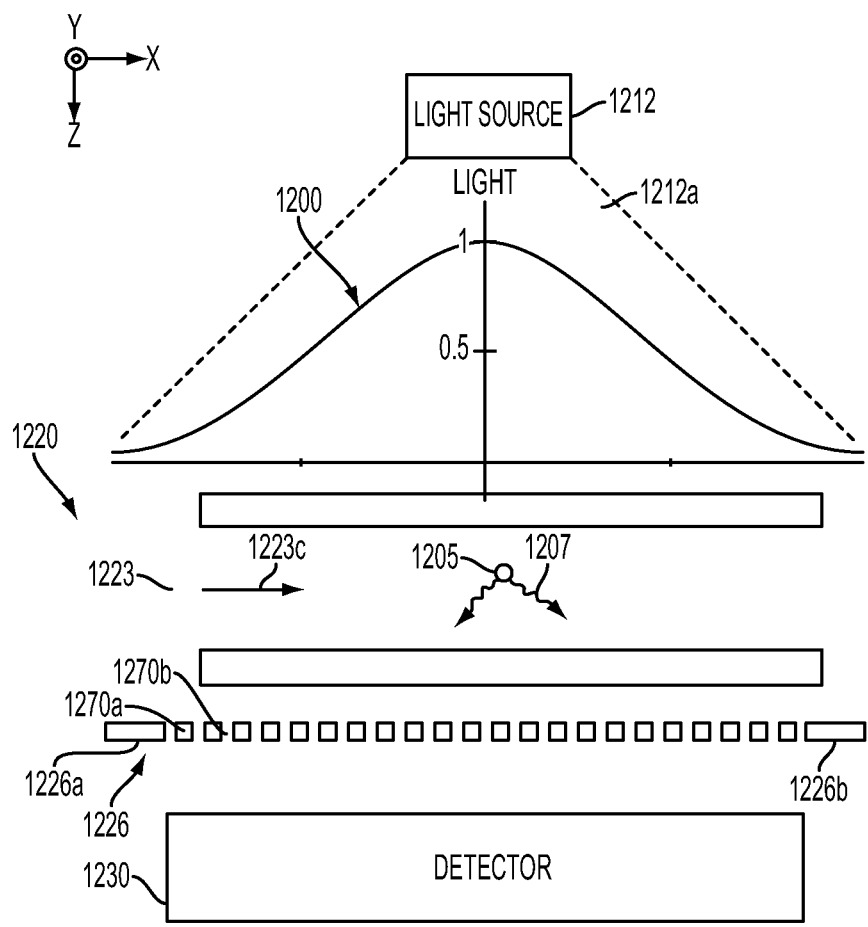
FIG. 12 illustrates a spatial modulation system that includes a spatial filter with mask features that have a length that is constant along the flow direction, the spatial filter used in conjunction with a light source with a Gaussian intensity distribution.

Some embodiments involve the use of a spatial filter wherein the length of the first and second features of the spatial filter is constant along the flow direction. In some cases the length of the first features is substantially equal to the length of the second features. FIG. 12 is a side view of a spatial filter 1226 that includes constant length features 1270a, 1270b arranged in relation to a light source 1212, fluidic device 1220, and a detector 1230. The spatial filter 1226 includes mask features including a number of first mask features 1270a that are more light transmissive and a number of second mask features 1270b that are less light transmissive. At least one object 1205 moves in the fluidic device 1220 along a flow direction 1223c and emanates light 1207. Although the object 1205 is illustrated as having a length in the x direction greater than the lengths of the mask features 1270a, 1270b, it will be understood that the length of the object 1205 may actually be smaller than at least some of the lengths of the mask features 1270a, 1270b.

FIG. 12 shows an intensity distribution 1200 of light 1212a emitted from a light source 1212 and distributed along the flow channel 1223 of the fluidic device 1210. In the embodiment shown, the intensity distribution 1200 of the light 1212a is approximately Gaussian. However, in other embodiments the intensity distribution may vary from the example embodiment illustrated.

Figure 13:
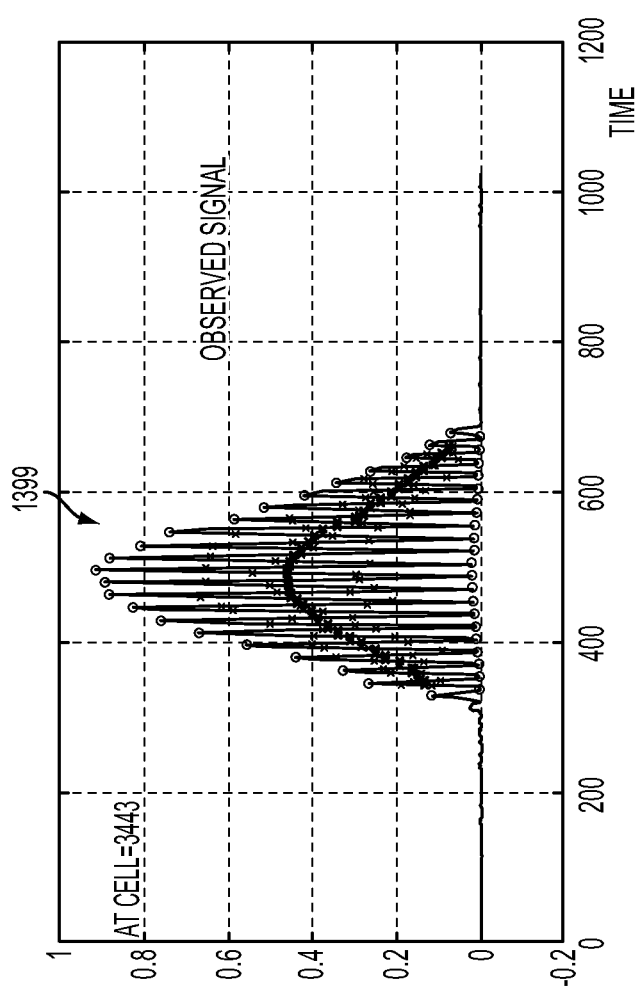
FIG. 13 is a graph of a signal generated by the detector of the system depicted in FIG. 12 as an object moves through the detection region.

FIG. 13 is a plot of an electrical signal 1399 that is generated by detector 1230 in response to sensing the modulated light emanating from an object 1205 moving along the flow path. The morphology of the electrical signal 1399 generated by the detector 1230 results from the intensity distribution 1200 of the light output 1212a from the light source 1212 and the interaction of the light 1212a with the mask features 1270a, 1270b, and object specific characteristics. As shown in FIG. 13, the output electrical signal 1399 generated by the detector 1230 includes a first set of positive going pulses of increasing amplitude having pulse widths (or duty cycle) that are substantially constant with respect to time and a set of negative going pulses of decreasing amplitude having pulse widths (or duty cycle) that are substantially constant with respect to time and equal to the pulse widths of the positive going pulses. The pulse frequency in this example is constant and can be used to determine the constant velocity of the object as it moves along the flow direction. The pulse widths of the electrical signal 1399 are a function of the velocity and the length of the object.

As shown, the amplitude of the positive going pulses in the output electrical signal 1399 is initially low between time t=0 and t=300 due to the distribution of the input light 1212a, as exhibited by intensity profile 1200, which has a lower intensity toward the edges 1226a, 1226b of the spatial filter 1226. The amplitude of the pulses increases for a time period due to the increase in the intensity of the input light 1212a (as illustrated by intensity profile 1200) before falling due to the decrease in the intensity of the input light 1212a.

A spatial filter pattern wherein the length of the first mask features d1 and the length of the second mask features d2 are both constant along the flow direction, where d1 may or may not be the same as d2, is called a periodic mask. In a periodic mask, the basic pattern is that of a periodically repeating identical cell units, where each cell unit is comprised of a pair of mask features: a first mask feature of length d1, followed by a second mask feature of length d2. In some approaches, a periodic mask where all the mask openings are the same (same width and height) may be used to determine object length along the flow direction.

Figure 14:
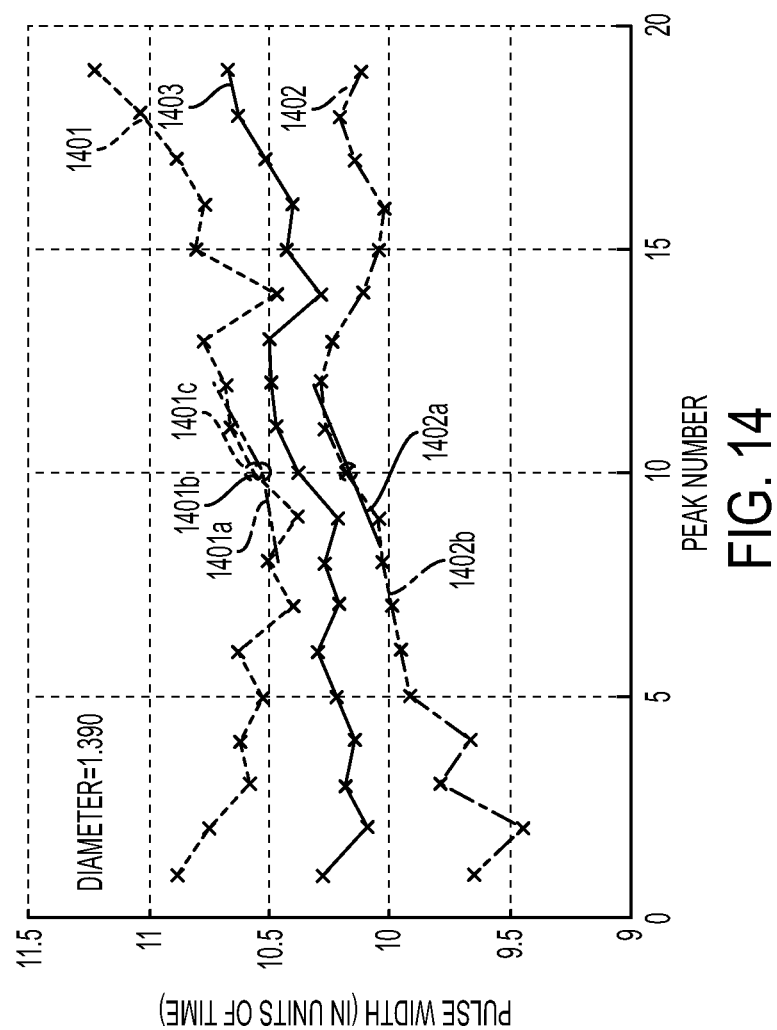
FIG. 14 illustrates a technique useful for determining object length using a spatial filter having periodic features of constant length along the longitudinal axis of the spatial filter.

The graph shown in FIG. 14 illustrates a technique for length determination of an object using a periodic mask. To measure the object properties such as the object length and velocity, a pulse width measured at a fraction 50% intensity can be used to measure the object velocity (because travel time of the object traversing a mask at 50% intensity is independent of the object dimensions, and is dependent the velocity of the object and the length of the mask feature). Simultaneously and independently of the object velocity measurement, the object length can be measured using the pulse widths away from the 50% maximum intensity (for example, at 20% maximum or minimum intensity) during "open" and "close" times, where the open times correspond to pulses that are generated when the emanating light from the object passes through a transparent mask feature and the close times correspond to pulses that are generated when the emanating light from the object is blocked by an opaque mask feature. Note that the pulses widths are measured in terms of time it takes the object to traverse an open (transmissive) or closed (opaque) mask feature.

In FIG. 14, curve 1401 plots the pulse widths at 20% maximum of the (positive) amplitude for the open features (positive pulses); curve 1402 plots the pulse widths at 20% minimum of the (negative) amplitude for the closed features (negative pulses); curve 1403 plots the averages of the pulse width values of curves 1401 and 1402.

In a scenario where (1) all the mask openings are identical, i.e., d1 is equal to d2; (2) the illumination is the same for each opening; and (3) the velocity is constant, the sum of each successive pair of open and close times should remain approximately the same. However, in many implementations, the three conditions listed above are not met. Due to the uneven (approximately Gaussian) light distribution on the spatial filter as shown in FIG. 12, the openings near the center of the mask receive much more light than the openings near the ends. The openings near the center are therefore the most accurate, and the particle length estimation accuracy deteriorates as the amount of illumination is reduced away from the center. Hence it is desirable to give more weight to the measurements near the center of the mask (with weights that roughly approximate the illumination profile).

In addition, there may be defect in one or more of the mask features or the fluidic device. Defects may occur, for example, if the laser used to cut the mask features may leave a ragged edge in one of the openings or if an opening got slightly covered during the manufacturing process. Hence the one defective mask feature may yield an erroneous measurement for the one defective feature. A defective mask feature is likely the cause for the obvious drop in measured open time for peak 14 in the graph of FIG. 14. However, the approaches discussed herein allow for identification and elimination of such defective measurements with little loss in overall accuracy.

Two measurements are taken from each open and close mask feature pair, e.g., the width at 20% of the maximum intensity for the positive going pulses and the width at 20% of the minimum intensity width for the negative going pulses. A simple average of the measurements may produce a suboptimal length estimate due to the non-uniformity of the light profile. Accordingly, in some implementations weighted curves are fit to the measured open and closed feature pulse widths, with weights corresponding to the illumination profile.

The points closer to the mask center (near peak 10, circled in the graph of FIG. 14) are given considerably more weight than the points at the ends. The fitted curves 1401a, 1402b, are illustrated near the center peak. The fitting also includes an algorithm to eliminate any mask/chip defects measurement points (such as RANSAC).

In FIG. 14, curve 1401 plots the pulse widths at 20% maximum of the (positive) intensity for the open features (positive pulses) and curve 1402 plots the pulse widths at 20% minimum of the (negative) intensity for the closed features (negative pulses). Curve 1401a plots the weighted fitted curve for the pulse widths for the positive pulses (open features) and curve 1402a plots the weighted fitted curve for the pulse widths for the negative pulses (closed features). Using the fitted curves 1401a, 1402a, an adjusted measurement of the open and close pulse width is computed, shown at peak 10 of FIG. 14. This adjustment slightly moves the measured points (e.g., from circle 1401b to circle 1401c for the open pulse width). Similarly, the measured point at peak 10 for the negative pulse widths 1402 is adjusted using the fitted curve 1402a. The object length is estimated from the adjusted open and close times. Note that the estimation of object length is based on all the available measurements, even though it is conceptually illustrated at peak 10 in FIG. 14.

For each opening, the average of open and close pulse widths corresponds to a point midway between open and close values, shown as points along curve 1403, the curve connecting the average points is the average curve 1403. Each average point on curve 1403 is (close time+open time)/2. Thus, twice the average value is the sum of (close time+open time), which should be roughly constant if the velocity is constant. Hence the average curve 1403 for an object that travels at a constant velocity through the channel should look like a horizontally flat line). In FIG. 14, the average curve 1403 is increasing over time, with a positive slope, which is an indication that the object is slowing as it travels across the spatial filter. The sloping average curve 1403 is the result of the situation that arises when the object takes successively more time to cross subsequent mask openings, on average. The slope of the average curve 1403 can therefore be used to tell whether the object is actually slowing or accelerating as it travels through the channel. In addition to the average object velocity information obtained from either the time or frequency domain signals, the spatial filter can be used to provide information about the instantaneous velocity of an object as it travels along the flow path, including whether the object is accelerating or slowing down, and by what amount, on a mask feature-by-feature basis.

The changes in velocity can also be visually demonstrated by flipping the signal 180 degrees and aligning the first and last minima points with the original signal to demonstrate that the peak centers do not align up (another indication of the object slowing), as discussed in connection with FIGS. 15A and 15B.

If multiple pulse width measurements are made for determining multiple object characteristics, e.g., both object length and velocity, the pulse width at two fractional values of the maximum (for positive pulses) or minimum (for negative pulses), e.g., 20% and 50% intensity can be simultaneously measured by setting two intensity thresholds, measuring four successive time points for each feature, and individually pairing the 20% and 50% points together.

Figure 15A:
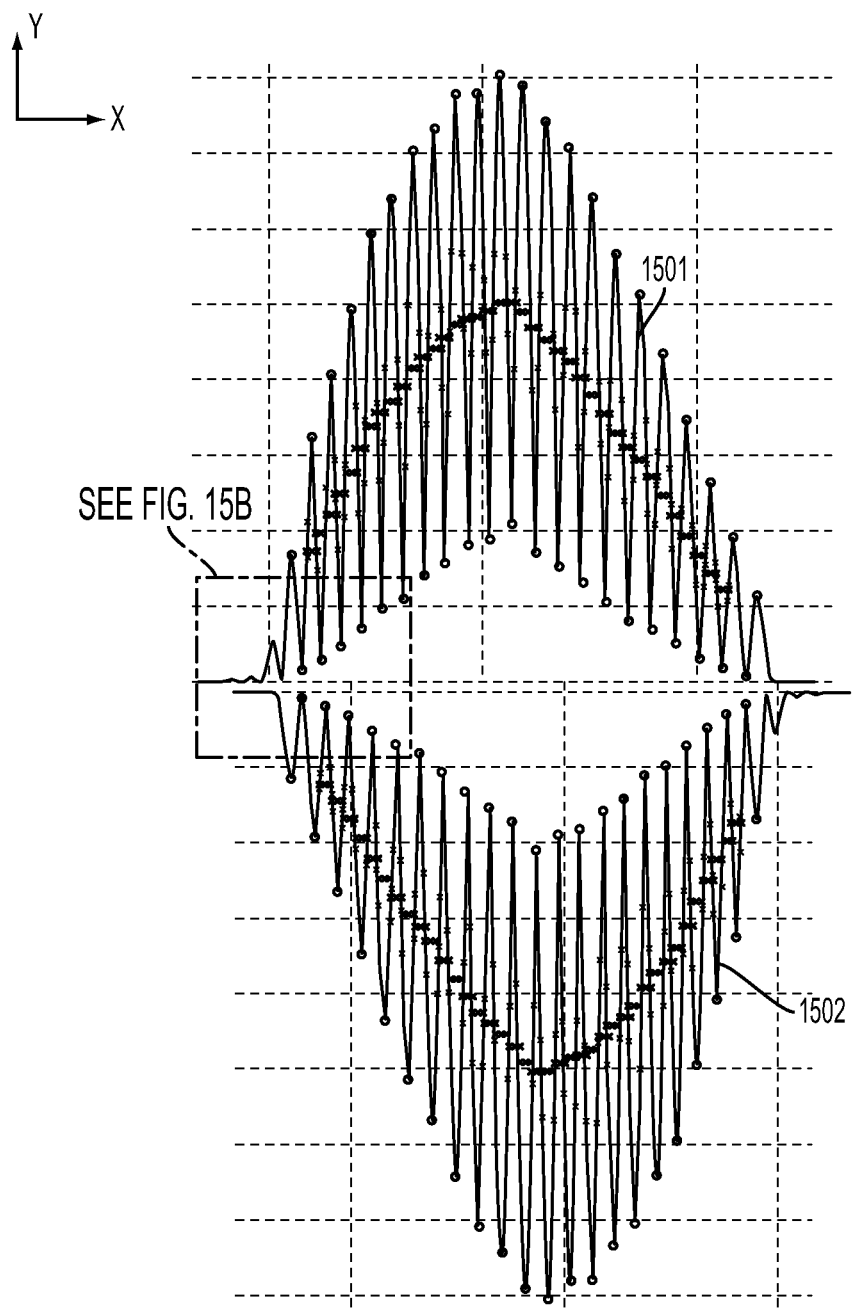
FIGS. 15A and 15B are graphs used to illustrate a process using the time varying detector signal for determining changes in velocity of an object as the object travels in the detection region.
Figure 15B:
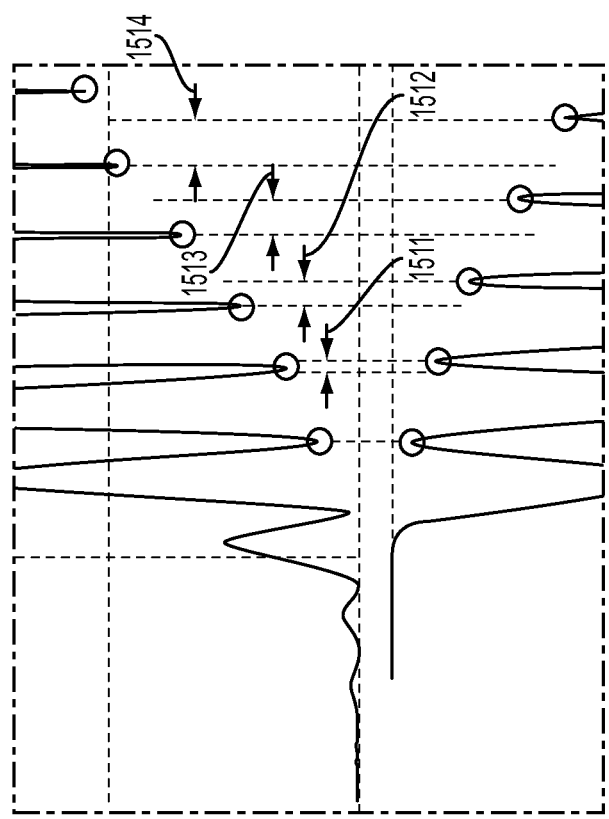

FIGS. 15A and 15B illustrate another process that may be implemented, e.g., by analysis circuitry 151 in FIG. 1. The process of FIGS. 15A and 15B uses the time varying signal from the detector to identify changes in an object's velocity as it traverses a detection region in a system having a spatial filter with constant length features. Graph 1501 illustrates a time varying signal generated by the detector as an object traverses the detection region. The positive peaks of time varying signal 1501 form an upper envelope that is Gaussian shape due to the Gaussian distribution of the light source that provides input light to the system.

Changes in the velocity of the object along the flow path can be detected by inverting the time varying signal 1501 along both the y and x axes y, forming inverted signal 1502. The distances between corresponding lower (or upper) peaks indicates that the object's velocity was changing. The distances can be used to determine the amount of velocity change as the object moves through the detection region. In the example provided by FIGS. 15A and 15B, the increasing offsets 1511, 1512, 1513, 1514 between corresponding lower peaks indicate that it takes more time for the object to reach successively further away peaks, hence the object velocity is decreasing (i.e., object is slowing down) as it moves through the detection region and the amount of the offsets 1511, 1512, 1513, 1514 can be used to determine the instantaneous velocity of the object at any given time and/or an amount of the velocity decrease.

Figure 16:
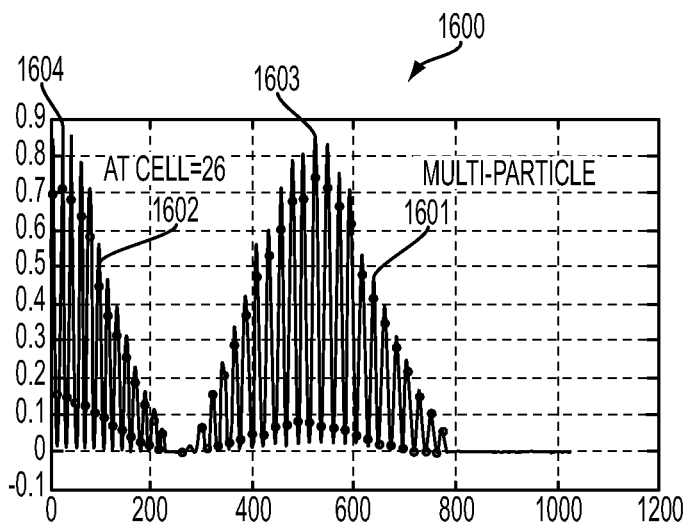
FIG. 16 shows a time varying detector signal having a shape indicative of two closely spaced objects traveling along a flow path.
Figure 17:
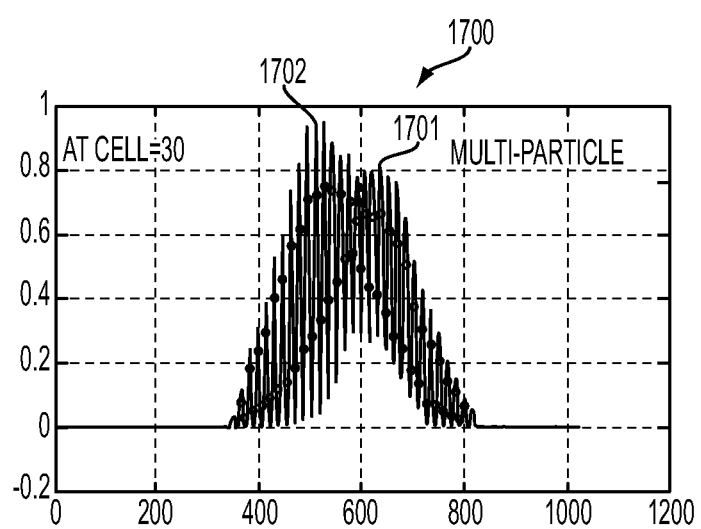
FIG. 17 shows a time varying detector signal having a shape indicative of two overlapping objects traveling along a flow path.
Figure 18:
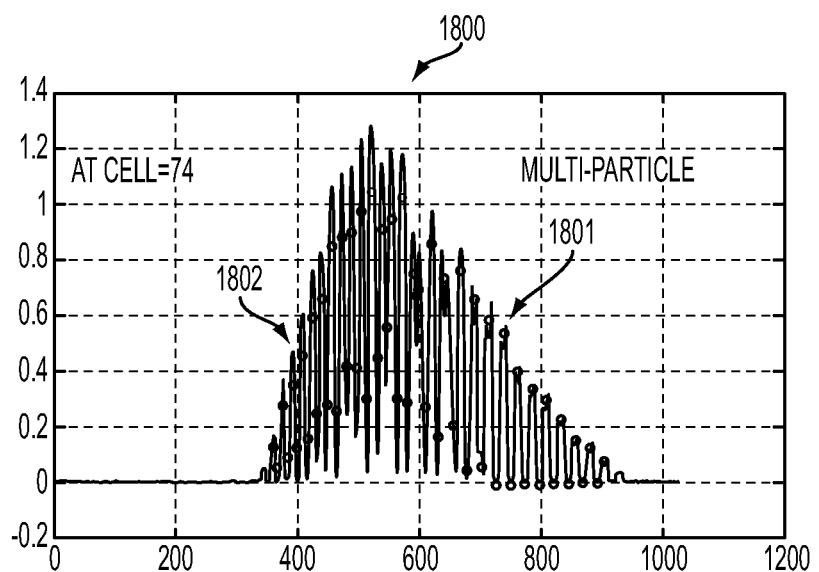
FIG. 18 shows a time varying detector signal having a shape indicative of two overlapping objects traveling along a flow path.

FIGS. 16-19 are screen captures of system output that illustrate processes that may be implemented, e.g., by analysis circuitry 151 in FIG. 1, to provide additional information about multiple objects that are in close proximity or that overlap along the flow direction as they move through the detection region. FIGS. 16-19 illustrate several cases of multiple particles in the detection region, where the particles are traveling separately (at some distance from each other), partially overlapping, or actually touching (aggregated) and moving together. The system may identify how the particles are moving together and the number of particles based on the wave shapes. For separate non-overlapping particles the system may independently determine the length of each particle. For example, as illustrated in FIG. 18, the system may identify that there are two particles in the detection area and that the first particle is traveling at a faster velocity than the second particle because the distance between peaks at t=400 is appreciably smaller than at t=800.

The processes illustrated by graphs 16-19 rely on analysis of the time varying signal generated by the detector. According to these processes, the shape of the time varying signal is analyzed to identify multiple objects overlapping or in close proximity in the detection portion of the flow path. Each of the graphs have an upper modulation envelope formed by the positive going peaks and a lower modulation envelope formed by the negative going peaks. The software algorithm detects multiple particles based on criteria described below and displays the recognition of multiple particles can display a text output such as "multi-particle" in the user interface display, as can be discerned in FIG. 16-19. In some implementations, discerning multiple objects in the detection region is performed by analyzing the upper and/or lower modulation envelopes of the graphs.

FIG. 16 shows a graph 1600 that has the characteristic shape indicating two objects flowing together in the detection region. Modulated light emanating from the first object creates portion 1601 of graph 1600 and modulated light emanating from the second object creates portion 1602 of graph 1600. The upper modulation envelope of graph 1600 exhibits two distinct peaks 1603, 1604 indicating the presence of two closely spaces objects. The distance between the first and second object is larger than the detection region, whereby the second object enters the detection region shortly after the first object has exited the detection region. The two particles travel in tandem, with the second object closely follows the first object in the flow path, but the objects are not overlapping, as indicated by the decrease to nearly zero of the upper modulation envelope between first 1601 and second 1602 graph portions. The first and second objects have approximately the same length along the flow direction as can be determined based on the approximately equal pulse widths of the graph 1600 in the first and second portions 1601, 1602. Even though a portion of the second object signal falls within the detection window in the frequency domain, the system can still distinguish from the time domain analysis that there are two objects in this case. In contrast, systems that lack a spatial filter mask as disclosed herein are prone to underestimating the number of objects by counting only one object instead of two in case of collisions (i.e., multiple particles in the detector region).

FIG. 17 illustrates a graph 1700 of the time varying detector signal having a shape indicative of two objects of approximately the same length that are overlapping in the detection region as they travel along the flow path. The upper envelope of graph 1700 includes two peaks 1701, 1702 corresponding to light emanating from the first and second objects, respectively. Light emanating from the first object that is detected concurrently with light emanating from the second object causes the lower modulation envelope of graph 1700 to be highly modulated. The second object enters the detection region shortly after the first object, and is slightly brighter that the first object as can be appreciated from the peak envelope 1702 being larger than 1701. Furthermore, the first and second objects are traveling at slightly different velocities. Initially the second object is in phase with the first object for the first few mask features, namely, the first and second objects enter and exit different mask features at roughly about the same time. Hence the two waveforms closely overlap, and the lower peak values are close to zero when the two objects are both simultaneously behind the less transmissive mask features. However, one object is traveling slightly faster than the other. Over time, the distance between the objects slowly changes such that the objects begin to go out of phase, i.e., one object enters a less transmissive mask feature while the other object enters a more transmissive mask feature. In the latter case, there is always at least on object visible through a less transmissive mask feature, and in consequence there is always some emanating light reaching the detector from either one of the objects. Hence the lower peaks of graph 1700 do not return to zero. The rate at which the objects go in and out of phase is dependent on the difference in their velocities. The closer the difference in object speed is, the slower the rate of going in and out of phase, and the longer time it would take to make the transition. In the case of FIG. 17, it takes almost up to t=600 before the objects are maximally out of phase, after which the particles begin to go back in phase, until they are finally back in phase by time t=750. The difference in object length and brightness also play a role in the resulting waveforms, although the most visible attribute is the interference pattern generated by the two objects traveling at slightly different speeds.

FIG. 18 illustrates a graph 1800 of the time varying detector signal having a shape indicative of two objects of approximately the same lengths that are overlapping in the detection region. Graph 1800 has a first portion 1801 that is predominantly caused by light emanating from the first object and a second portion 1802 that is predominantly caused by light emanating from the second object. The situation is similar to the case depicted in FIG. 17. However, in FIG. 17 the two objects are traveling at nearly the same velocity, only slightly different. In contrast, the objects in FIG. 18 are traveling at appreciably different speeds. The different object velocities are indicated by the different pulse widths in the first 1801 and second 1802 portions of the graph 1800. The first object 1802 is traveling at a higher speed as can be discerned from the higher frequency of the pulses of graph 1800 in the time interval t=400 to t=500. The second object, however, is traveling at a slower speed than the first object based on the lower frequency of the graph 1800 in the time interval t=700 to t=900. A lower frequency implies that it takes more time for the second object to pass the same mask feature lengths as the first object. Since the velocity difference is considerably larger than in FIG. 17, the two objects are going in and out of phase much more rapidly, hence the pattern of non-zero negative peaks is more complex, containing not one but several out-of-phase regions.

Figure 19:
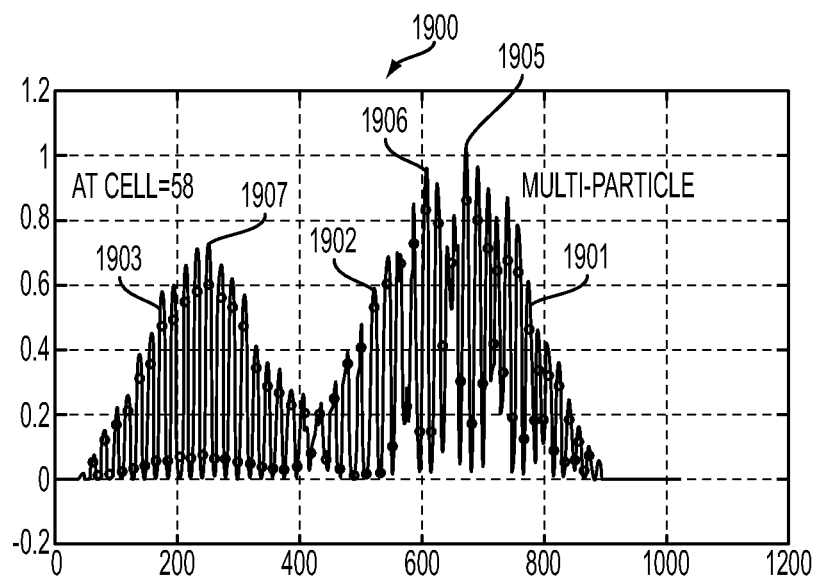
FIG. 19 shows a time varying detector signal having a shape indicative of three overlapping and/or closely spaced objects traveling along a flow path.

FIG. 19 illustrates a graph 1900 of the time varying detector signal having a shape indicative of three objects of approximately the same length traveling in close proximity in the detection region. The first object enters the detection region first at about time t=50. The other two objects are overlapping in the detection region and following closely behind the first object, starting at about time t=400. The presence of the first object that partially overlaps at least the second object is indicated by portion 1903 of graph 1900. The presence of the second and third objects that are partially overlapping is indicated by portions 1901, 1902 of graph 1900, respectively. Light emanating from the first, second, and third objects produces separate peaks 1905, 1906, 1907 of the upper modulation envelope. The constructive interference pattern of going in and out of phase between the second and third objects of portions 1901 and 1902 is similar to the situation if FIG. 18, with the exception that the object 1902 is traveling at a lower velocity than 1901 (the reverse of FIG. 18). In addition, the overlap situation between the first object 1903 and pair of overlapping objects 1902 and 1901 is similar to that in FIG. 17 except that one object in FIG. 17 is now replaced with a pair of overlapping object in FIG. 19.

The use of a spatial filter can provide the ability to accurately measure object length and velocity using a single detector in a high throughput cytometry settings. The system can tell, based on the resulting waveforms exactly how many objects are traveling in the channel, whether each object is accelerating or slowing down, and how many objects overlap and by how much. In consequence, the system may be able to much more accurately count how many objects have truly passed in the detection region, including overlapping objects, and provide robust information about each object length and velocity. In contrast, existing systems that lack a spatial filter mask as disclosed herein are prone to underestimating the number of objects by counting only one object instead of two or more in cases of collisions (i.e., multiple particles in the detector region). Furthermore, the knowledge of each object length and velocity can be used to eliminate objects outside the range of interest, for example objects that are too large or too small (in terms of the length), or traveling at too high or too slow speeds, etc., which could not be members of the particular objects of interest (e.g., a particular bacteria species, or beads of certain size).

In some implementations, the velocity of the objects can be determined by calculating an average of the positive and negative going pulse widths in the pulse pairs. The velocity of the object is related to the slope of the averages with respect to a pulse (or mask feature) number.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

The invention claimed is:

1. A system, comprising:
a spatial filter having a plurality of mask features;
at least one detector positioned to sense light emanating from at least one object moving in a flow path along a flow direction, an intensity of the sensed light being time modulated according to the mask features, the detector configured to generate a time varying electrical signal comprising a sequence of pulses in response to the sensed light; and
an analyzer configured to:
measure a pulse width of at least some of the pulses at a fraction of an amplitude extremum of the pulses and to determine a length of the object along the flow direction based on the measured pulse widths, and predict an expected pulse width measurement of a hypothesized mask feature of length x based on the measured pulse width.

2. The system of claim 1, wherein:
the mask features include first features and second features; and
the first features are substantially transparent and the second features are substantially opaque.

3. The system of claim 1, wherein the analyzer is configured to:
determine a function, $f(\{p_i\},x)$ that fits a set of mask feature measurement points $\{p_i\}$, each point given by $p_i=(x_i,y_i)$, where each $x_i$ is associated with a feature length of an $i^{th}$ mask feature and each $y_i$ is associated with an $i^{th}$ measured pulse width associated with the $i^{th}$ mask feature, the function predicting an expected pulse width measurement of a hypothesized mask feature of length x based on the set of mask feature measurement points $\{p_i\}$.

4. The system of claim 3, wherein the function is a linear function.

5. The system of claim 4, wherein:
the mask features include first features and second features;
the first mask features are substantially optically transparent and the second mask features are substantially optically opaque; and
extrapolating the object length using the function comprises determining $f(\{p_i\}, \text{for } x=0)$.

6. The system of claim 5, wherein the mask features are arranged so that a length of the mask features changes linearly along the flow direction.

7. The system of claim 5, wherein the mask features are arranged so that a length of the mask features changes non-linearly along the flow direction.

8. The system of claim 3, wherein the function is an exponential or logarithmic function.

9. The system of claim 8, wherein the mask features are arranged so that the length of the mask features changes logarithmically along the flow direction.

10. The system of claim 1, wherein a frequency of the mask features is constant along the flow direction and corresponds to a fixed pitch value.

11. The system of claim 1, wherein the fraction of the pulse extremum is in a range of about 10% to 40% or about 60% to 90%.

12. The system of claim 1, wherein:
the mask features include a first section arranged in a first linear chirp or logarithmic chirp pattern and a second section arranged in a second linear or logarithmic chirp pattern, wherein the first pattern and the second pattern are symmetrical around a center line extending laterally across the spatial filter;
the first mask features are substantially transparent and the second mask features are substantially opaque and the transparent features have a first specified length proximate to the center line; and
the transparent features of the first pattern have a linear decrease in length of a second specified value along the flow direction and the transparent features of the second pattern have a linear increase in length of the second specified value along the flow direction.

13. The system of claim 1, further comprising a light source configured to provide input light, wherein the light emanating from the objects is responsive to the input light.

14. The system of claim 1 wherein the intensity distribution of the input light is approximately Gaussian or Lambertian.

15. The system of claim 1, wherein:
the mask features include first features and second features, a length of the first features is constant along the flow direction of the spatial filter and a length of the second features is constant along the flow direction of the spatial filter;
the analyzer is configured to:
measure pulse widths of positive going pulses;
measure pulse widths of negative going pulses; and
determine the length of the object based on averages of widths of pulse pairs, each pulse pair comprising a positive pulse and an adjacent negative pulse.

16. The system of claim 15, wherein the analyzer is further configured to determine whether a velocity of the object is increasing or decreasing based on a slope of the averages of the pulse width pairs.

17. The system of claim 1, wherein:
a length of the first features is constant along the flow direction of the spatial filter;
a length of the second features is constant along the flow direction of the spatial filter;
the at least one object comprises multiple objects;
the detector is positioned to sense light emanating from the multiple objects moving in a flow path along the flow direction;
the analyzer is configured to:
measure pulse widths of positive going pulses;
measure pulse widths of negative going pulses; and
identify a number of the multiple objects traveling together along the flow path based on the pulse widths of the positive pulses and the negative pulses.

18. The system of claim 17, wherein the analyzer is configured to determine a distance between two or more objects traveling together based on the pulse widths of the positive pulses and the negative pulses.

19. The system of claim 1, wherein the analyzer is configured to determine an instantaneous velocity of the object as the object travels along the flow path relative to the mask features based on the measured pulse widths.

20. The system of claim 1, wherein the analyzer is configured to determine, on a mask feature-by-feature basis, whether the object is speeding up or slowing down as the object travels along the flow path based on the measured pulse widths.

21. A method, comprising:
sensing light emanating from at least one object moving in a flow path along a flow direction of a spatial filter, the spatial filter having a plurality of mask features comprising first features alternating with second features along the flow direction, the first features having first light-transmission characteristics and the second features having second light transmission characteristics, different from the first light transmission characteristics, an intensity of the sensed light being time modulated according to the mask features;
generating a time varying electrical signal comprising a plurality of time modulated pulses in response to the sensed light;
measuring pulse widths of the pulses at a fraction of a maximum extremum of the pulses;
determining a length of the object along the flow direction based on the measured pulse widths; and
predicting an expected pulse width measurement of a hypothesized mask feature of length x based on the measured pulse width.

22. The method of claim 21, wherein determining the length of the object comprises:
determining a function, $f(\{p_i\},x)$ that fits the set of mask feature measurement points $\{p_i\}$, each point given by $p_i=(x_i,y_i)$, where each $x_i$ is associated with a feature length of an $i^{th}$ mask feature and $y_i$ is associated with an $i^{th}$ measured pulse width associated with the $i^{th}$ mask feature; the function predicting an expected pulse width measurement of an hypothesized mask feature of length x based on the mask feature measurement points $\{p_i\}$; and
extrapolating the object length using the function.

23. The method of claim 22, further comprising removing outliers in measurement points $\{p_i\}$ before determining the function, the outliers corresponding to erroneous measurements.

24. The method of claim 22, wherein extrapolating the object length using the function comprises determining $f(\{p_i\}, \text{for } x=0)$.

25. The method of claim 21, wherein:
a length of the first features is constant along the flow direction of the spatial filter;
a length of the second features is constant along the flow direction of the spatial filter;
measuring the pulse width of each of the pulses comprises:
measuring pulse widths of positive pulses;
measuring pulse widths of negative pulses; and
determining the length of the object along the flow direction comprises determining the length of the object based on averages of widths of pulses in pulse pairs, each pulse pair comprising a positive pulse and an adjacent negative pulse.

26. The method of claim 21, wherein:
the at least one object comprises multiple objects;
sensing the emanating light comprise sensing light emanating from the multiple objects;
measuring the pulse widths comprises:
measuring pulse widths of positive going pulses;
measuring pulse widths of negative going pulses; and
identifying a number of the multiple objects traveling together along the flow path based on the pulse widths of the positive going pulses and the negative going pulses.

27. The method of claim 26, further comprising determining a distance along the flow direction between two or more objects traveling at a velocity based on the pulse widths of the positive pulses and the negative pulses.

28. The method of claim 21, further comprising determining an instantaneous velocity of the object as the mask moves along the flow path past the mask features based on the measured pulse widths.

29. A system, comprising:
a spatial filter having a plurality of mask features;
at least one detector positioned to sense light emanating from at least one object moving in a flow path along a flow direction, an intensity of the sensed light being time modulated according to the mask features, the detector configured to generate a time varying electrical signal comprising a sequence of pulses in response to the sensed light; and
an analyzer configured to:
measure a pulse width of at least some of the pulses at in a range of about 10% to 40% or 60% to 90% of an amplitude extremum of the pulses,
predict an expected pulse width measurement of a hypothesized mask feature of length x based on the measured pulse width, and
determine, based on the pulse widths, one or more of:
a length along the flow direction of the object;
an instantaneous velocity of the object;
whether the object is accelerating or decelerating.

* * * * *